United States Patent
Matsumura et al.

(10) Patent No.: US 8,530,692 B2
(45) Date of Patent: Sep. 10, 2013

(54) COMPOUND, FLUORINE-CONTAINING POLYMER, RADIATION-SENSITIVE RESIN COMPOSITION AND METHOD FOR PRODUCING COMPOUND

(75) Inventors: Nobuji Matsumura, Tokyo (JP); Yuusuke Asano, Tokyo (JP); Hirokazu Sakakibara, Tokyo (JP); Yukio Nishimura, Tokyo (JP); Takehiko Naruoka, Tokyo (JP)

(73) Assignee: JSR Corporation, Tokyo (JP)

( * ) Notice: Subject to any disclaimer, the term of this patent is extended or adjusted under 35 U.S.C. 154(b) by 0 days.

(21) Appl. No.: 13/216,209

(22) Filed: Aug. 23, 2011

(65) Prior Publication Data
US 2012/0100480 A1    Apr. 26, 2012

Related U.S. Application Data

(63) Continuation of application No. PCT/JP2010/052682, filed on Feb. 23, 2010.

(30) Foreign Application Priority Data
Feb. 23, 2009    (JP) .................. 2009-039085

(51) Int. Cl.
C07C 68/00    (2006.01)
C07C 69/96    (2006.01)
C08F 20/28    (2006.01)
G03F 7/039    (2006.01)

(52) U.S. Cl.
USPC ............................ 560/219; 560/205; 560/220

(58) Field of Classification Search
None
See application file for complete search history.

(56) References Cited

U.S. PATENT DOCUMENTS

| | | | |
|---|---|---|---|
| 5,744,537 A | 4/1998 | Brunsvold et al. | |
| 2004/0005512 A1* | 1/2004 | Mizutani et al. | 430/270.1 |
| 2005/0014090 A1 | 1/2005 | Hirayama et al. | |
| 2005/0277059 A1 | 12/2005 | Kanda | |

FOREIGN PATENT DOCUMENTS

| | | |
|---|---|---|
| EP | 0159428 | 10/1985 |
| JP | 59-093448 | 5/1984 |
| JP | 5-188598 | 7/1993 |
| JP | 6-012452 B2 | 2/1994 |
| JP | 2002-220416 | 8/2002 |
| JP | 2004-004227 | 1/2004 |
| JP | 2004-004576 | 1/2004 |
| JP | 2004-012510 | 1/2004 |
| JP | 2005-173474 | 6/2005 |
| JP | 2005-309376 | 11/2005 |
| JP | 2005-352384 | 12/2005 |
| JP | 2006-048029 | 2/2006 |
| JP | 2007-204385 | 8/2007 |
| JP | 2008-115102 | 5/2008 |
| WO | WO 2004/068242 | 8/2004 |
| WO | WO 2009/087889 | 7/2009 |
| WO | WO 2009/142181 | 11/2009 |
| WO | WO 2009/142183 | 11/2009 |

OTHER PUBLICATIONS

International Preliminary Report on Patentability with Written Opinion of the International Searching Authority for corresponding International Application No. PCT/JP2010/052682, Sep. 13, 2011.
International Search Report for corresponding International Application No. PCT/JP2010/052682, Apr. 6, 2010.
Chinese Office Action for corresponding CN Application No. 201080008657.2, Jun. 4, 2013.

* cited by examiner

*Primary Examiner* — Yevegeny Valenrod
(74) *Attorney, Agent, or Firm* — Ditthavong Mori & Steiner, P.C.

(57) ABSTRACT

A compound has a following general formula (1).

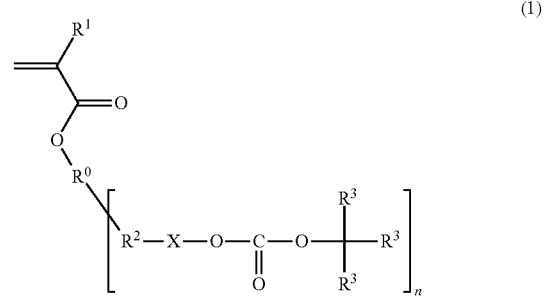

$R^0$ represents an (n+1)-valent linear or branched aliphatic hydrocarbon group having 1 to 10 carbon atoms, or the like. $R^1$ represents a hydrogen atom, a methyl group, or a trifluoromethyl group. $R^2$ represents a single bond or the like. $R^3$ represent a linear or branched alkyl group having 1 to 4 carbon atoms or the like. X represents a linear or branched fluoroalkylene group having 1 to 10 carbon atoms, and n is an integer from 1 to 5.

11 Claims, 1 Drawing Sheet

COMPOUND, FLUORINE-CONTAINING POLYMER, RADIATION-SENSITIVE RESIN COMPOSITION AND METHOD FOR PRODUCING COMPOUND

CROSS-REFERENCE TO RELATED APPLICATIONS

The present application is a continuation application International Application No. PCT/JP2010/052682, filed Feb. 23, 2010, which claims priority to Japanese Patent Application No. 2009-039085, filed Feb. 23, 2009. The contents of these applications are incorporated herein by reference in their entirety.

BACKGROUND OF THE INVENTION

1. Field of the Invention

The invention relates to a compound, a fluorine-containing polymer, and a radiation-sensitive resin composition.

2. Discussion of the Background

In the field of microfabrication (e.g., production of integrated circuit devices), lithographic technology that enables microfabrication with a line width of 0.10 µm or less has been desired to achieve a higher degree of integration.

Therefore, use of radiation having a shorter wavelength has been studied in order to implement microfabrication with a line width of 0.10 µm or less. Examples of radiation having a short wavelength include deep ultraviolet rays (e.g., mercury lamp bright line spectrum and excimer laser light), X-rays, electron beams, and the like. In particular, KrF excimer laser light (wavelength: 248 nm) and ArF excimer laser light (wavelength: 193 nm) have attracted attention.

As a resist that is suitable for excimer laser light, various resists (chemically-amplified resists) that utilize a chemical amplification effect due to an acid-dissociable functional group-containing component and a component that generates an acid upon irradiation (exposure) (hereinafter may be referred to as "acid generator") have been proposed.

For example, a chemically-amplified resist that includes a resin containing a t-butyl ester group of a carboxylic acid or a t-butyl carbonate group of phenol, and an acid generator has been proposed. This resist utilizes a phenomenon in which the t-butyl ester group or the t-butyl carbonate group contained in the resin dissociates due to an acid generated upon exposure to form an acidic group (e.g., carboxyl group or phenolic hydroxyl group), so that the exposed area of the resist film becomes readily soluble in an alkaline developer.

Such a lithographic process will be required to form a finer pattern (e.g., a resist pattern with a line width of about 90 nm). A pattern having a line width of less than 90 nm may be formed by reducing the wavelength of the light source of the exposure system, or increasing the numerical aperture (NA) of the lens.

In recent years, liquid immersion lithography has been proposed as lithographic technology. In liquid immersion lithography, a liquid refractive medium (immersion liquid) (e.g., purified water or fluorine-containing inert liquid) is interposed (at least over the resist film) between the lens and the resist film formed on the substrate during exposure.

According to liquid immersion lithography, the optical space (path) is filled with a liquid (e.g., pure water) having a high refractive index (n) instead of an inert gas (e.g., air or nitrogen) so that the resolution can be increased without causing a decrease in depth of focus in the same manner as in the case of using a short-wavelength light source or a high NA lens. A resist pattern that exhibits excellent resolution and an excellent depth of focus can be inexpensively formed by liquid immersion lithography using a lens provided in an existing system. A polymer, an additive, and the like for forming a resist used for liquid immersion lithography have been proposed (see WO04/068242, Japanese Patent Application Publication (KOKAI) No. 2005-173474 and Japanese Patent Application Publication (KOKAI) No. 2006-48029, for example).

SUMMARY OF THE INVENTION

According to one aspect of the present invention, a compound has a general formula (1).

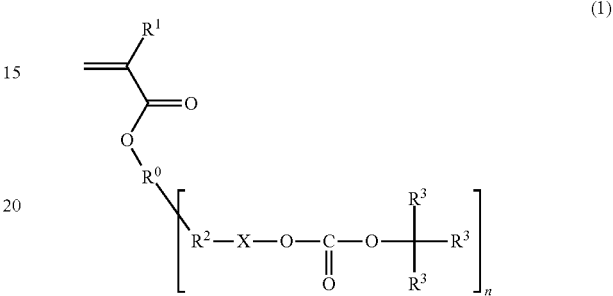

n is an integer from 1 to 5. $R^0$ represents an (n+1)-valent linear or branched aliphatic hydrocarbon group having 1 to 10 carbon atoms, an (n+1)-valent alicyclic hydrocarbon group having 3 to 20 carbon atoms, or an (n+1)-valent aromatic hydrocarbon group having 6 to 20 carbon atoms. $R^1$ represents a hydrogen atom, a methyl group, or a trifluoromethyl group. $R^2$ represents a single bond, a methylene group, an ethylene group, a 1-methylethylene group, a 2-methylethylene group, or a divalent alicyclic hydrocarbon group having 4 to 20 carbon atoms. Each $R^2$ is a same as or different from each other when n is 2 or more. Each $R^3$ independently represents a monovalent alicyclic hydrocarbon group having 4 to 20 carbon atoms or a linear or branched alkyl group having 1 to 4 carbon atoms. Or each $R^3$ independently represents a monovalent alicyclic hydrocarbon group having 4 to 20 carbon atoms or a linear or branched alkyl group having 1 to 4 carbon atoms, and two of $R^3$ groups bond to form a divalent alicyclic hydrocarbon group having 4 to 20 carbon atoms together with the carbon atom bonded to the two of $R^3$ groups. X represents a linear or branched fluoroalkylene group having 1 to 10 carbon atoms. Each X is a same as or different from each other when n is 2 or more.

According to another aspect of the present invention, a fluorine-containing polymer includes a repeating unit shown by a general formula (I).

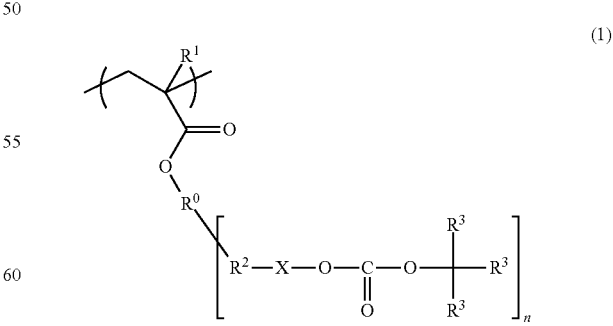

n is an integer from 1 to 5. $R^0$ represents an (n+1)-valent linear or branched aliphatic hydrocarbon group having 1 to 10 carbon atoms, an (n+1)-valent alicyclic hydrocarbon group having 3 to 20 carbon atoms, or an (n+1)-valent aromatic hydrocarbon group having 6 to 20 carbon atoms. $R^1$ represents a hydrogen atom, a methyl group, or a trifluoromethyl group. $R^2$ represents a single bond, a methylene group, an ethylene group, a 1-methylethylene group, a 2-methylethylene group, or a divalent alicyclic hydrocarbon group having 4 to 20 carbon atoms. Each $R^2$ is a same as or different from each other when n is 2 or more. Each $R^3$ independently represents a monovalent alicyclic hydrocarbon group having 4 to 20 carbon atoms or a linear or branched alkyl group having 1 to 4 carbon atoms. Or each $R^3$ independently represents a monovalent alicyclic hydrocarbon group having 4 to 20 carbon atoms or a linear or branched alkyl group having 1 to 4 carbon atoms, and two of $R^3$ groups bond to form a divalent alicyclic hydrocarbon group having 4 to 20 carbon atoms together with the carbon atom bonded to the two of $R^3$ groups. X represents a linear or branched fluoroalkylene group having 1 to 10 carbon atoms. Each X is a same as or different from each other when n is 2 or more.

According to further aspect of the present invention, a method of producing a compound includes reacting a compound shown by a general formula (1-0) with a compound shown by a general formula (0).

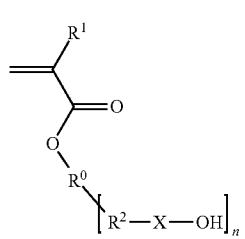
(1-0)

n is an integer from 1 to 5. $R^0$ represents an (n+1)-valent linear or branched aliphatic hydrocarbon group having 1 to 10 carbon atoms, an (n+1)-valent alicyclic hydrocarbon group having 3 to 20 carbon atoms, or an (n+1)-valent aromatic hydrocarbon group having 6 to 20 carbon atoms. $R^1$ represents a hydrogen atom, a methyl group, or a trifluoromethyl group. $R^2$ represents a single bond, a methylene group, an ethylene group, a 1-methylethylene group, a 2-methylethylene group, or a divalent alicyclic hydrocarbon group having 4 to 20 carbon atoms. Each $R^2$ is a same as or different from each other when n is 2 or more. X represents a linear or branched fluoroalkylene group having 1 to 10 carbon atoms. Each X is a same as or different from each other when n is 2 or more.

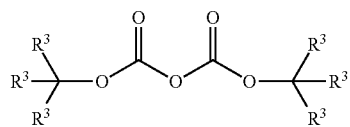
(0)

Each $R^3$ independently represents a monovalent alicyclic hydrocarbon group having 4 to 20 carbon atoms or a linear or branched alkyl group having 1 to 4 carbon atoms. Or each $R^3$ independently represents a monovalent alicyclic hydrocarbon group having 4 to 20 carbon atoms or a linear or branched alkyl group having 1 to 4 carbon atoms, and two of $R^3$ groups bond to form a divalent alicyclic hydrocarbon group having 4 to 20 carbon atoms together with the carbon atom bonded to the two of $R^3$ groups.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings.

DESCRIPTION OF THE EMBODIMENTS

Figure 1:
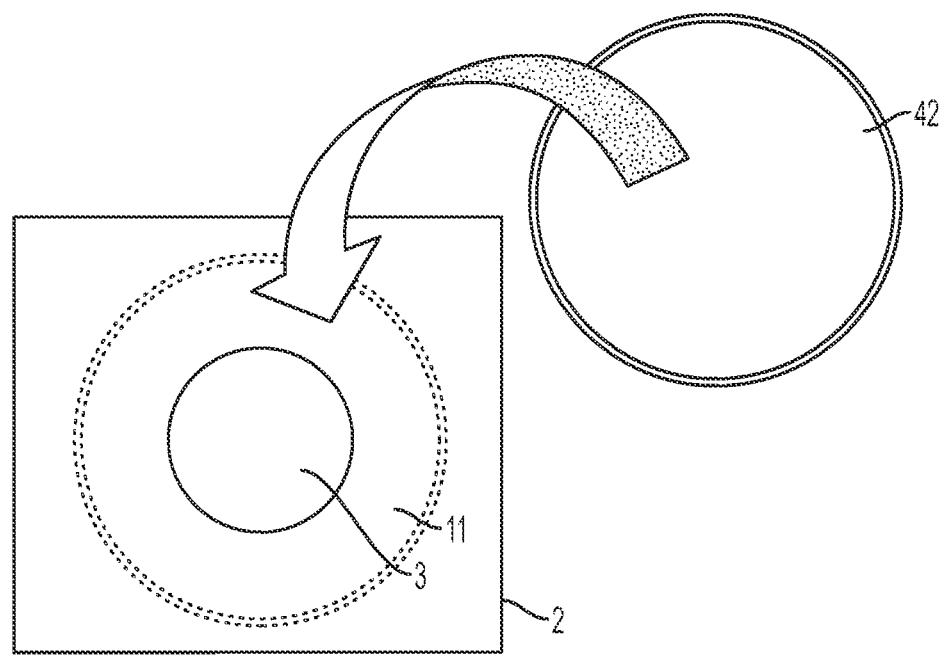
FIG. 1 is a schematic view showing an example of a state in which a resist film is caused to come in contact with ultrapure water.

Several embodiments of the invention provide the following compound, method of producing the same, fluorine-containing polymer, and radiation-sensitive resin composition.

[1] A compound shown by a general formula (1),

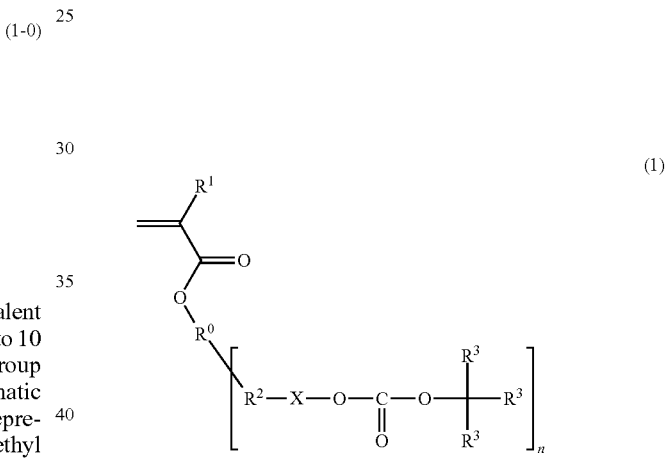
(1)

wherein $R^0$ represents an (n+1)-valent linear or branched aliphatic hydrocarbon group having 1 to 10 carbon atoms, an (n+1)-valent alicyclic hydrocarbon group having 3 to 20 carbon atoms, or an (n+1)-valent aromatic hydrocarbon group having 6 to 20 carbon atoms, $R^1$ represents a hydrogen atom, a methyl group, or a trifluoromethyl group, $R^2$ represents a single bond, a methylene group, an ethylene group, a 1-methylethylene group, a 2-methylethylene group, or a divalent alicyclic hydrocarbon group having 4 to 20 carbon atoms, provided that $R^2$ may be the same or different when a plurality of $R^2$ are present, $R^3$ individually represent a monovalent alicyclic hydrocarbon group having 4 to 20 carbon atoms or a linear or branched alkyl group having 1 to 4 carbon atoms, provided that two of $R^3$ may bond to form a divalent alicyclic hydrocarbon group having 4 to 20 carbon atoms together with the carbon atom bonded thereto, X represents a linear or branched fluoroalkylene group having 1 to 10 carbon atoms, provided that X may be the same or different when a plurality of X are present, and n is an integer from 1 to 5.

[2] The compound according to [1], the compound being shown by a general formula (1a),

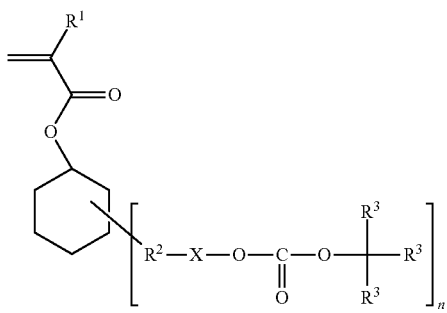

wherein $R^1$ represents a hydrogen atom, a methyl group, or a trifluoromethyl group, $R^2$ represents a single bond, a methylene group, an ethylene group, a 1-methylethylene group, a 2-methylethylene group, or a divalent alicyclic hydrocarbon group having 4 to 20 carbon atoms, provided that $R^2$ may be the same or different when a plurality of $R^2$ are present, $R^3$ individually represent a monovalent alicyclic hydrocarbon group having 4 to 20 carbon atoms or a linear or branched alkyl group having 1 to 4 carbon atoms, provided that two of $R^3$ may bond to form a divalent alicyclic hydrocarbon group having 4 to 20 carbon atoms together with the carbon atom bonded thereto, X represents a linear or branched fluoroalkylene group having 1 to 10 carbon atoms, provided that X may be the same or different when a plurality of X are present, and n is an integer from 1 to 5.

[3] The compound according to [1] or [2], wherein n is 2.

[4] The compound according to [3], the compound being shown by a general formula (1-2),

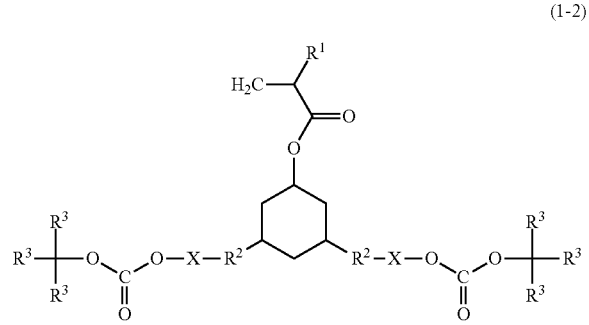

wherein $R^1$ represents a hydrogen atom, a methyl group, or a trifluoromethyl group, $R^2$ represents a single bond, a methylene group, an ethylene group, a 1-methylethylene group, a 2-methylethylene group, or a divalent alicyclic hydrocarbon group having 4 to 20 carbon atoms, $R^3$ individually represent a monovalent alicyclic hydrocarbon group having 4 to 20 carbon atoms or a linear or branched alkyl group having 1 to 4 carbon atoms, provided that two of $R^3$ may bond to form a divalent alicyclic hydrocarbon group having 4 to 20 carbon atoms together with the carbon atom bonded thereto, and X represents a linear or branched fluoroalkylene group having 1 to 10 carbon atoms.

[5] A fluorine-containing polymer including a repeating unit (1) derived from the compound according to any one of [1] to [4].

[6] A fluorine-containing polymer including a repeating unit shown by a general formula (I),

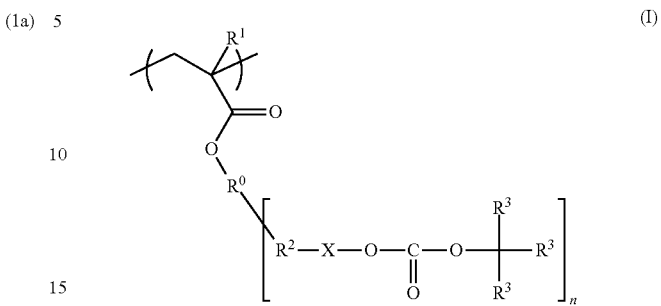

wherein $R^0$ represents an (n+1)-valent linear or branched aliphatic hydrocarbon group having 1 to 10 carbon atoms, an (n+1)-valent alicyclic hydrocarbon group having 3 to 20 carbon atoms, or an (n+1)-valent aromatic hydrocarbon group having 6 to 20 carbon atoms, $R^1$ represents a hydrogen atom, a methyl group, or a trifluoromethyl group, $R^2$ represents a single bond, a methylene group, an ethylene group, a 1-methylethylene group, a 2-methylethylene group, or a divalent alicyclic hydrocarbon group having 4 to 20 carbon atoms, $R^3$ individually represent a monovalent alicyclic hydrocarbon group having 4 to 20 carbon atoms or a linear or branched alkyl group having 1 to 4 carbon atoms, provided that two of $R^3$ may bond to form a divalent alicyclic hydrocarbon group having 4 to 20 carbon atoms together with the carbon atom bonded thereto, X represents a linear or branched fluoroalkylene group having 1 to 10 carbon atoms, n is an integer from 1 to 5.

[7] The fluorine-containing polymer according to [6], wherein the repeating unit shown by the general formula (I) is a repeating unit shown by a general formula (Ia),

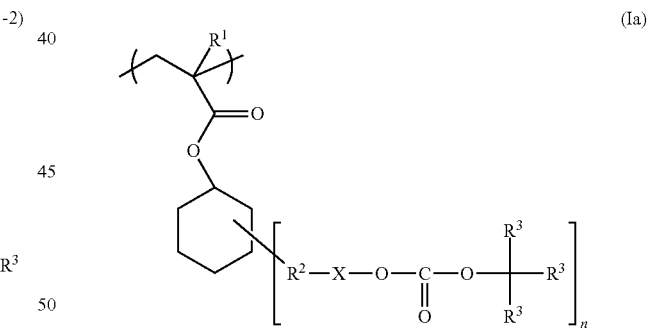

wherein $R^1$ represents a hydrogen atom, a methyl group, or a trifluoromethyl group, $R^2$ represents a single bond, a methylene group, an ethylene group, a 1-methylethylene group, a 2-methylethylene group, or a divalent alicyclic hydrocarbon group having 4 to 20 carbon atoms, $R^3$ individually represent a monovalent alicyclic hydrocarbon group having 4 to 20 carbon atoms or a linear or branched alkyl group having 1 to 4 carbon atoms, provided that two of $R^3$ may bond to form a divalent alicyclic hydrocarbon group having 4 to 20 carbon atoms together with the carbon atom bonded thereto, X represents a linear or branched fluoroalkylene group having 1 to 10 carbon atoms, n is an integer from 1 to 5.

[8] The fluorine-containing polymer according to [7], wherein the repeating unit shown by the general formula (Ia) is a repeating unit shown by a general formula (I-2),

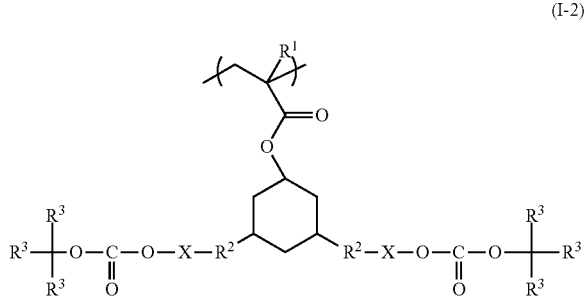

(I-2)

wherein $R^1$ represents a hydrogen atom, a methyl group, or a trifluoromethyl group, $R^2$ represents a single bond, a methylene group, an ethylene group, a 1-methylethylene group, a 2-methylethylene group, or a divalent alicyclic hydrocarbon group having 4 to 20 carbon atoms, $R^3$ individually represent a monovalent alicyclic hydrocarbon group having 4 to 20 carbon atoms or a linear or branched alkyl group having 1 to 4 carbon atoms, provided that two of $R^3$ may bond to form a divalent alicyclic hydrocarbon group having 4 to 20 carbon atoms together with the carbon atom bonded thereto, and X represents a linear or branched fluoroalkylene group having 1 to 10 carbon atoms.

[9] A radiation-sensitive resin composition including (A) the fluorine-containing polymer according to any one of [5] to [8], and (B) an acid-labile group-containing polymer (excluding the fluorine-containing polymer (A)).

[10] The radiation-sensitive resin composition according to [9], wherein the content of the fluorine-containing polymer (A) in the composition is 0.1 to 40 parts by mass based on 100 parts by mass of the acid-labile group-containing polymer (B).

[11] A method of producing a compound including reacting a compound shown by a general formula (1-0) with a compound shown by a general formula (0),

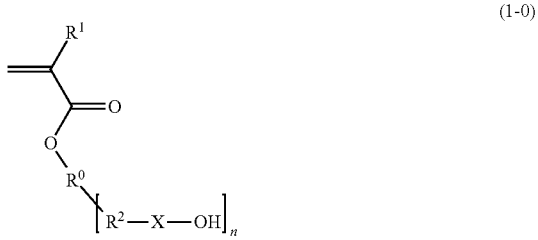

(1-0)

wherein $R^0$ represents an (n+1)-valent linear or branched aliphatic hydrocarbon group having 1 to 10 carbon atoms, an (n+1)-valent alicyclic hydrocarbon group having 3 to 20 carbon atoms, or an (n+1)-valent aromatic hydrocarbon group having 6 to 20 carbon atoms, $R^1$ represents a hydrogen atom, a methyl group, or a trifluoromethyl group, $R^2$ represents a single bond, a methylene group, an ethylene group, a 1-methylethylene group, a 2-methylethylene group, or a divalent alicyclic hydrocarbon group having 4 to 20 carbon atoms, provided that $R^2$ may be the same or different when a plurality of $R^2$ are present, X represents a linear or branched fluoroalkylene group having 1 to 10 carbon atoms, provided that X may be the same or different when a plurality of X are present, and n is an integer from 1 to 5,

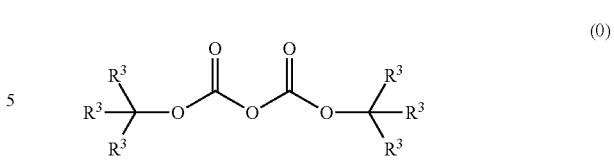

(0)

wherein $R^3$ individually represent a monovalent alicyclic hydrocarbon group having 4 to 20 carbon atoms or a linear or branched alkyl group having 1 to 4 carbon atoms, provided that two of $R^3$ may bond to form a divalent alicyclic hydrocarbon group having 4 to 20 carbon atoms together with the carbon atom bonded thereto.

The above compound produces a polymer component used for a radiation-sensitive resin composition that may suitably be used for liquid immersion lithography.

The above fluorine-containing polymer produces a polymer component used for a radiation-sensitive resin composition that may suitably be used for liquid immersion lithography.

The above radiation-sensitive resin composition may suitably be used as a resist for liquid immersion lithography that exposes a resist film through an immersion liquid (e.g., water).

The above method can easily synthesize a compound that produces a polymer component used for a radiation-sensitive resin composition that may suitably be used for liquid immersion lithography.

The embodiments will now be described with reference to the accompanying drawings, wherein like reference numerals designate corresponding or identical elements throughout the various drawings. Exemplary embodiments of the invention are described below. Note that the invention is not limited to the following exemplary embodiments. Various modifications and improvements may be made of the following exemplary embodiments without departing from the scope of the invention based on the knowledge of a person having ordinary skill in the art. Note that the term "(meth)acryl" used herein refers to at least one of the terms "acryl" and "methacryl".

I. Compound

A compound according to one embodiment of the invention is shown by the following general formula (1), and forms a fluorine-containing polymer according to one embodiment of the invention (described below). Since the compound according to one embodiment of the invention includes a specific fluoroalkylene group in the molecule, a radiation-sensitive resin composition that includes a polymer component including a fluorine-containing polymer that includes a repeating unit (1) (i.e., repeating unit (I)) derived from the compound according to one embodiment of the invention can sufficiently increase the receding contact angle formed by a resist film and an immersion liquid. Moreover, the radiation-sensitive resin composition can reduce the elution volume of a substance eluted into an immersion liquid (e.g., water) upon contact with the immersion liquid during liquid immersion lithography, and can suppress occurrence of watermarks (W/M) and bubble defects that may occur due to liquid immersion lithography.

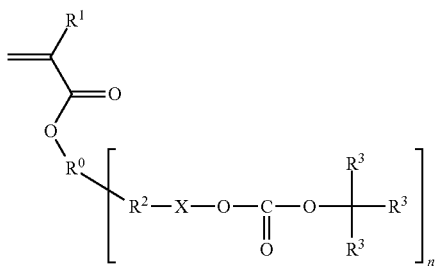

(1)

wherein $R^0$ represents an (n+1)-valent linear or branched aliphatic hydrocarbon group having 1 to 10 carbon atoms, an (n+1)-valent alicyclic hydrocarbon group having 3 to 20 carbon atoms, or an (n+1)-valent aromatic hydrocarbon group having 6 to 20 carbon atoms, $R^1$ represents a hydrogen atom, a methyl group, or a trifluoromethyl group, $R^2$ represents a single bond, a methylene group, an ethylene group, a 1-methylethylene group, a 2-methylethylene group, or a divalent alicyclic hydrocarbon group having 4 to 20 carbon atoms, provided that $R^2$ may be the same or different when a plurality of $R^2$ are present, $R^3$ individually represent a monovalent alicyclic hydrocarbon group having 4 to 20 carbon atoms or a linear or branched alkyl group having 1 to 4 carbon atoms, provided that two of $R^3$ may bond to form a divalent alicyclic hydrocarbon group having 4 to 20 carbon atoms together with the carbon atom bonded thereto, X represents a linear or branched fluoroalkylene group having 1 to 10 carbon atoms, provided that X may be the same or different when a plurality of X are present, and n is an integer from 1 to 5.

Examples of the (n+1)-valent linear or branched aliphatic hydrocarbon group having 1 to 10 carbon atoms represented by $R^1$ in the general formula (1) include a group obtained by elimination of (n+1) hydrogen atoms from an aliphatic hydrocarbon having 1 to 10 carbon atoms (e.g., methane, ethane, propane, butane, 2-methylpropane, pentane, 2-methylbutane, neopentane, hexane, heptane, octane, nonane, or decane), and the like.

Examples of the (n+1)-valent alicyclic hydrocarbon group having 3 to 20 carbon atoms include a group obtained by elimination of (n+1) hydrogen atoms from an alicyclic hydrocarbon (e.g., cyclobutane, cyclopentane, cyclohexane, bicyclo[2.2.1]heptane, bicyclo[2.2.2]octane, tricyclo[5.2.1.0$^{2,6}$]decane, or tricyclo[3.3.1.1$^{3,7}$]decane), and the like. Examples of the (n+1)-valent aromatic hydrocarbon group having 6 to 20 carbon atoms include a group obtained by elimination of (n+1) hydrogen atoms from an aromatic hydrocarbon (e.g., benzene or naphthalene), and the like.

Examples of the divalent alicyclic hydrocarbon group having 4 to 20 carbon atoms represented by $R^2$ in the general formula (1) include divalent hydrocarbon groups including an alicyclic ring derived from a cycloalkane such as cyclobutane, cyclopentane, cyclohexane, bicyclo[2.2.1]heptane, bicyclo[2.2.2]octane, tricyclo[5.2.1.0$^{2,6}$]decane, tetracyclo[6.2.1.1$^{3,6}$.0$^{2,7}$]dodecane, or tricycle[3.3.1.1$^{3,7}$]decane. Note that $R^2$ may represent a group (derivative) obtained by substituting at least one hydrogen atom of the divalent alicyclic hydrocarbon group with at least one of a linear or branched alkyl group having 1 to 4 carbon atoms (e.g., methyl group, ethyl group, n-propyl group, i-propyl group, n-butyl group, 2-methylpropyl group, 1-methylpropyl group, or t-butyl group), a cycloalkyl group, a hydroxyl group, a cyano group, a hydroxyalkyl group having 1 to 10 carbon atoms, a carboxyl group, an oxygen atom, and the like.

Examples of the monovalent alicyclic hydrocarbon group having 4 to 20 carbon atoms represented by $R^3$ in the general formula (1) include groups including an alicyclic ring derived from a cycloalkane (e.g., norbornane, tricyclodecane, tetracyclododecane, adamantane, cyclobutane, cyclopentane, cyclohexane, cycloheptane, or cyclooctane), and the like. Note that $R^3$ may represent a group obtained by substituting the alicyclic hydrocarbon group with at least one of a linear or branched alkyl group having 1 to 4 carbon atoms (e.g., methyl group, ethyl group, n-propyl group, i-propyl group, n-butyl group, 2-methylpropyl group, 1-methylpropyl group, or t-butyl group) and a cycloalkyl group.

Examples of the divalent alicyclic hydrocarbon group having 4 to 20 carbon atoms that is formed by two of $R^3$ in the general formula (1) together with the carbon atom bonded thereto (i.e., the carbon atom bonded to the oxygen atom) include cycloalkylene groups such as a cyclobutylene group, a cyclopentylene group, a cyclohexylene group, and a cyclooctylene group. Note that the divalent alicyclic hydrocarbon group may be a group (derivative) obtained by substituting a cycloalkylene group with at least one of a linear or branched alkyl group having 1 to 4 carbon atoms (e.g., methyl group, ethyl group, n-propyl group, i-propyl group, n-butyl group, 2-methylpropyl group, 1-methylpropyl group, or t-butyl group) and a cycloalkyl group.

Examples of the linear or branched alkyl group having 1 to 4 carbon atoms represented by $R^3$ in the general formula (1) include a methyl group, an ethyl group, an n-propyl group, an i-propyl group, an n-butyl group, a 2-methylpropyl group, a 1-methylpropyl group, a t-butyl group, and the like.

Preferable examples of the group represented by —C($R^3$)$_3$ in the general formula (1) include a t-butyl group, a 1-n-(1-ethyl-1-methyl)propyl group, a 1-n-(1,1-dimethyl)propyl group, a 1-n-(1,1-dimethyl)butyl group, a 1-n-(1,1-dimethyl)pentyl group, 1-(1,1-diethyl)propyl group, a 1-n-(1,1-diethyl)butyl group, a 1-n-(1,1-diethyl)pentyl group, a 1-(1-methyl)cyclopentyl group, a 1-(1-ethyl)cyclopentyl group, a 1-(1-n-propyl)cyclopentyl group, a 1-(1-i-propyl)cyclopentyl group, a 1-(1-methyl)cyclohexyl group, a 1-(1-ethyl)cyclohexyl group, a 1-(1-n-propyl)cyclohexyl group, a 1-(1-i-propyl)cyclohexyl group, a 1-[1-methyl-1-(2-norbornyl)]ethyl group, a 1-[1-methyl-1-(2-tetracyclodecanyl)]ethyl group, a 1-[1-methyl-1-(1-adamantyl)]ethyl group, a 2-(2-methyl)norbornyl group, a 2-(2-ethyl)norbornyl group, a 2-(2-n-propyl)norbornyl group, a 2-(2-i-propyl)norbornyl group, a 2-(2-methyl)tetracyclodecanyl group, a 2-(2-ethyl)tetracyclodecanyl group, a 2-(2-n-propyl)tetracyclodecanyl group, a 2-(2-i-propyl)tetracyclodecanyl group, a 2-(2-methyl)adamantyl group, a 2-(2-ethyl)adamantyl group, a 2-(2-n-propyl)adamantyl group, a 2-(2-i-propyl)adamantyl group, a group obtained by substituting such a group with at least one of a linear or branched alkyl group having 1 to 4 carbon atoms (e.g., methyl group, ethyl group, n-propyl group, i-propyl group, n-butyl group, 2-methylpropyl group, 1-methylpropyl group, or t-butyl group) or a cycloalkyl group, and the like.

Examples of the linear or branched fluoroalkylene group having 1 to 10 carbon atoms represented by X in the general formula (1) include the fluoroalkylene groups shown by the following formulas (X-1) to (X-8), and the like. Among these, a (ditrifluoromethyl)methylene group (i.e., the fluoroalkylene group shown by the formula (X-1)) is particularly preferable.

(X-1)
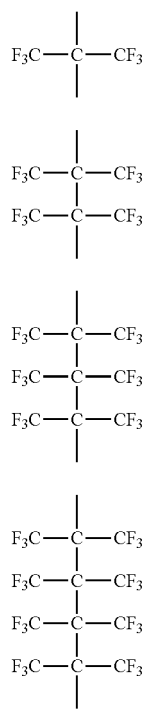
(X-2)
(X-3)
(X-4)
(X-5)
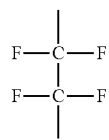
(X-6)
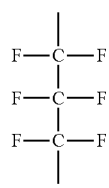
(X-7)
(X-8)
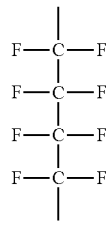
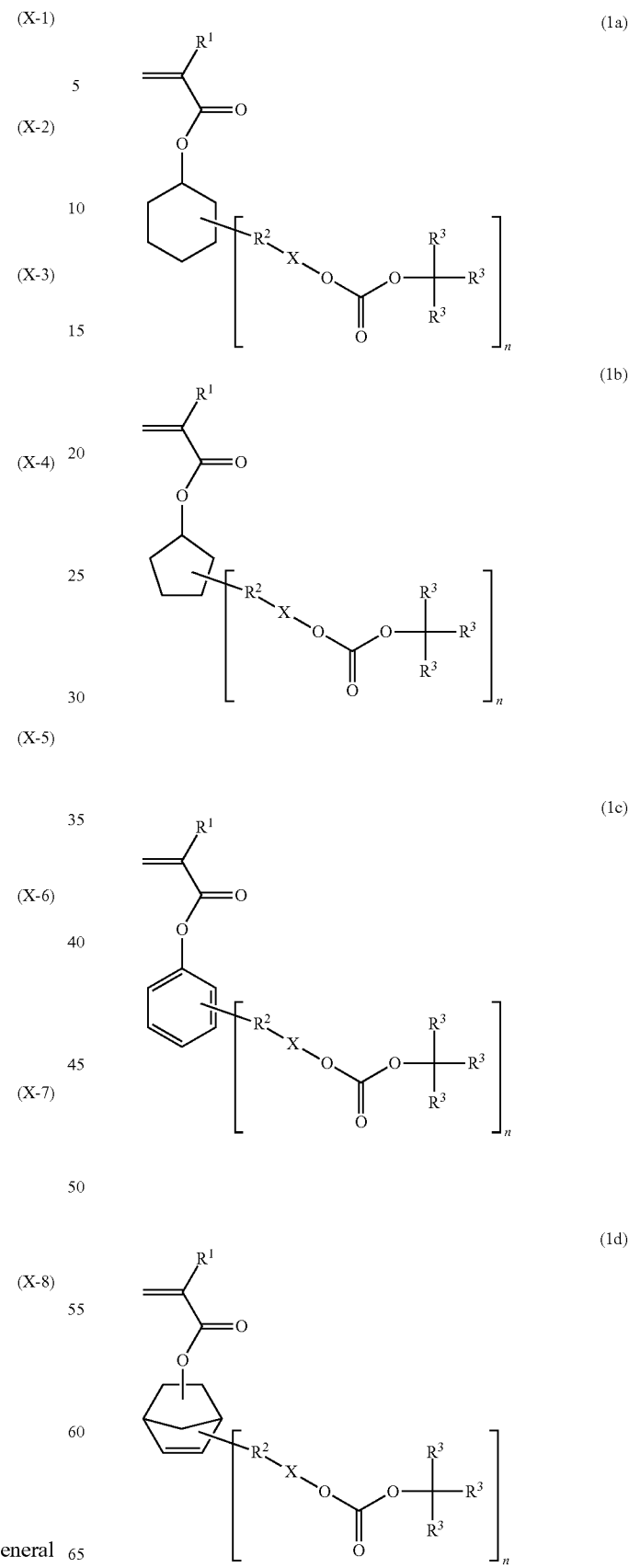
Specific examples of the compound shown by the general formula (1) include compounds shown by the following general formulas (1a) to (1f).

-continued

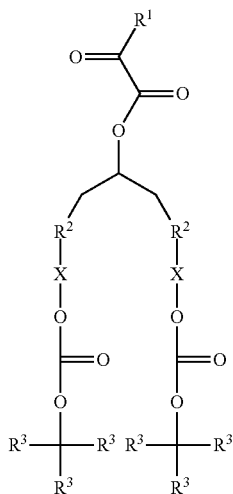
(1e)

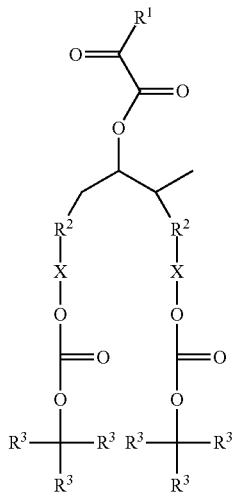
(1f)

wherein $R^1$ represents a hydrogen atom, a methyl group, or a trifluoromethyl group, $R^2$ represents a single bond, a methylene group, an ethylene group, a 1-methylethylene group, a 2-methylethylene group, or a divalent alicyclic hydrocarbon group having 4 to 20 carbon atoms, provided that $R^2$ may be the same or different when a plurality of $R^2$ are present, $R^3$ individually represent a monovalent alicyclic hydrocarbon group having 4 to 20 carbon atoms or a linear or branched alkyl group having 1 to 4 carbon atoms, provided that two of $R^3$ may bond to form a divalent alicyclic hydrocarbon group having 4 to 20 carbon atoms together with the carbon atom bonded thereto, X represents a linear or branched fluoroalkylene group having 1 to 10 carbon atoms, provided that X may be the same or different when a plurality of X are present, and n is an integer from 1 to 5.

The compound according to one embodiment of the invention is preferably a compound shown by the general formula (1a) (i.e., a compound shown by the general formula (1) wherein $R^0$ represents a group derived from (n+1)-valent cyclohexane), more preferably a compound shown by the general formula (1) wherein n is 2, and particularly preferably a compound shown by the following general formula (1-2).

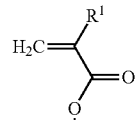
(1-2)

wherein $R^1$ represents a hydrogen atom, a methyl group, or a trifluoromethyl group, $R^2$ individually represent a single bond, a methylene group, an ethylene group, a 1-methylethylene group, a 2-methylethylene group, or a divalent alicyclic hydrocarbon group having 4 to 20 carbon atoms, $R^3$ individually represent a monovalent alicyclic hydrocarbon group having 4 to 20 carbon atoms or a linear or branched alkyl group having 1 to 4 carbon atoms, provided that two of $R^3$ may bond to form a divalent alicyclic hydrocarbon group having 4 to 20 carbon atoms together with the carbon atom bonded thereto, and X individually represent a linear or branched fluoroalkylene group having 1 to 10 carbon atoms.

II. Method of Producing Compound

A method of producing the compound according to one embodiment of the invention includes reacting a compound shown by the following general formula (1-0) with a compound shown by the following general formula (0). Note that the compound according to one embodiment of the invention is not limited to a compound produced by the above method. The compound according to one embodiment of the invention can be easily synthesized by the above method. Note that the compounds are preferably reacted in an appropriate solvent in the presence of an amine.

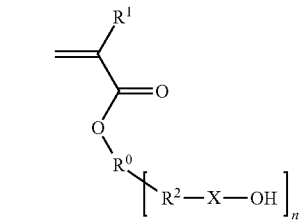
(1-0)

wherein $R^0$ represents an (n+1)-valent linear or branched aliphatic hydrocarbon group having 1 to 10 carbon atoms, an (n+1)-valent alicyclic hydrocarbon group having 3 to 20 carbon atoms, or an (n+1)-valent aromatic hydrocarbon group having 6 to 20 carbon atoms, $R^1$ represents a hydrogen atom, a methyl group, or a trifluoromethyl group, $R^2$ represents a single bond, a methylene group, an ethylene group, a 1-methylethylene group, a 2-methylethylene group, or a divalent alicyclic hydrocarbon group having 4 to 20 carbon atoms, provided that $R^2$ may be the same or different when a plurality of $R^2$ are present, X represents a linear or branched fluoroalkylene group having 1 to 10 carbon atoms, provided that X may be the same or different when a plurality of X are present, and n is an integer from 1 to 5.

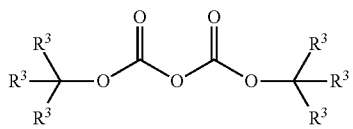

(0)

wherein $R^3$ individually represent a monovalent alicyclic hydrocarbon group having 4 to 20 carbon atoms or a linear or branched alkyl group having 1 to 4 carbon atoms, provided that two of $R^3$ may bond to form a divalent alicyclic hydrocarbon group having 4 to 20 carbon atoms together with the carbon atom bonded thereto.

The description given above in connection with $R^0$, $R^1$, $R^2$, and X in the general formula (1) is applied to $R^0$, $R^1$, $R^2$, and X in the general formula (1-0). The description given above in connection with $R^3$ in the general formula (1) is applied to $R^3$ in the general formula (0).

Examples of the amine include, but are not limited to, triethylamine, 1,4-diazabicyclo[2.2.2]octane, pyridine, and the like.

The reaction temperature is preferably −15 to 100° C., more preferably 0 to 80° C., and particularly preferably 20 to 70° C. The compounds may be reacted in the air, but are preferably reacted in an inert gas atmosphere (e.g., nitrogen or argon).

The compound may be purified by distillation or column chromatography.

The compound according to one embodiment of the invention may suitably be used as a monomer component that forms the fluorine-containing polymer according to one embodiment of the invention.

III. Fluorine-Containing Polymer

1. Components

A fluorine-containing polymer according to one embodiment of the invention includes a repeating unit (1) derived from the compound according to one embodiment of the invention described in the section entitled "I. Compound" (hereinafter may be referred to as "repeating unit (1)"). Specific examples of the repeating unit (1) include a repeating unit (I) shown by the following general formula (I) (hereinafter may be referred to as "repeating unit (I)"). Note that it is preferable that a film (coating) formed using only the fluorine-containing polymer have a receding contact angle of 70° or more, more preferably 72° or more, and particularly preferably 75° or more. Note that the term "receding contact angle" used herein refers to the contact angle formed by a liquid surface and a substrate when dripping 25 μl of water onto a substrate on which a film (resist film) is formed, and sucking the water on the substrate at a rate of 10 μl/min. The receding contact angle may be measured using a contact angle meter ("DSA-10" manufactured by KRUS), for example.

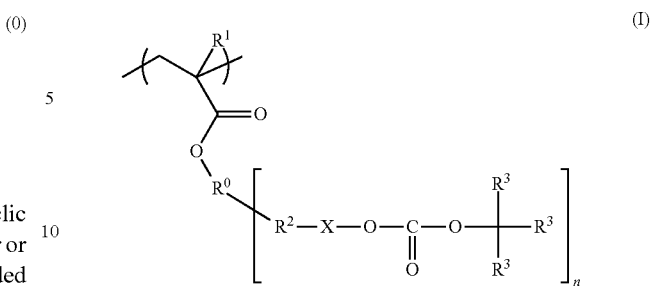

(I)

wherein $R^0$ represents an (n+1)-valent linear or branched aliphatic hydrocarbon group having 1 to 10 carbon atoms, an (n+1)-valent alicyclic hydrocarbon group having 3 to 20 carbon atoms, or an (n+1)-valent aromatic hydrocarbon group having 6 to 20 carbon atoms, $R^1$ represents a hydrogen atom, a methyl group, or a trifluoromethyl group, $R^2$ represents a single bond, a methylene group, an ethylene group, a 1-methylethylene group, a 2-methylethylene group, or a divalent alicyclic hydrocarbon group having 4 to 20 carbon atoms, provided that $R^2$ may be the same or different when a plurality of $R^2$ are present, $R^3$ individually represent a monovalent alicyclic hydrocarbon group having 4 to 20 carbon atoms or a linear or branched alkyl group having 1 to 4 carbon atoms, provided that two of $R^3$ may bond to form a divalent alicyclic hydrocarbon group having 4 to 20 carbon atoms together with the carbon atom bonded thereto, X represents a linear or branched fluoroalkylene group having 1 to 10 carbon atoms, provided that X may be the same or different when a plurality of X are present, and n is an integer from 1 to 5.

Specific examples of the repeating unit shown by the general formula (I) include repeating units shown by the following general formulas (I-1) to (I-6).

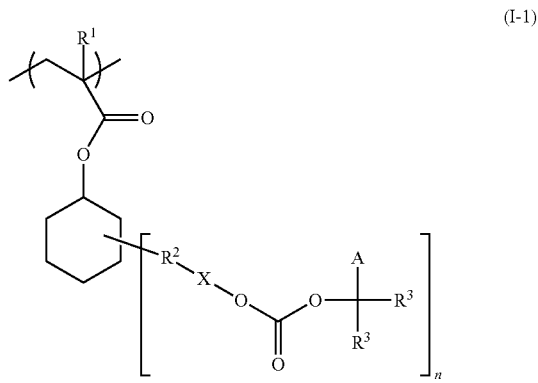

(I-1)

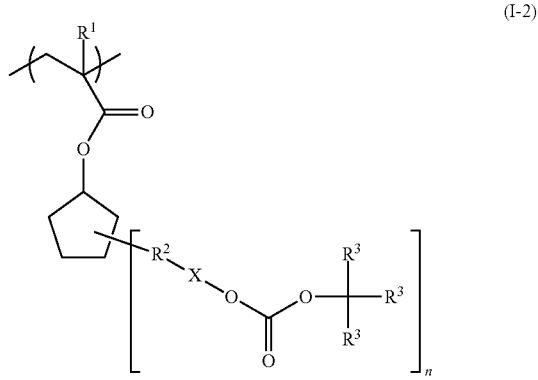

(I-2)

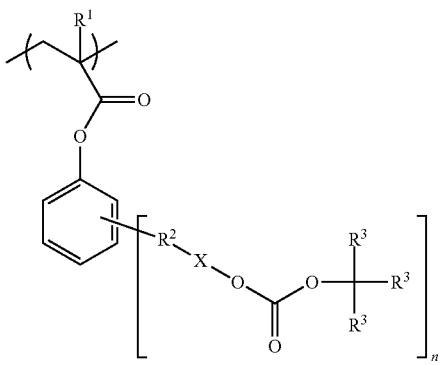

(I-3)

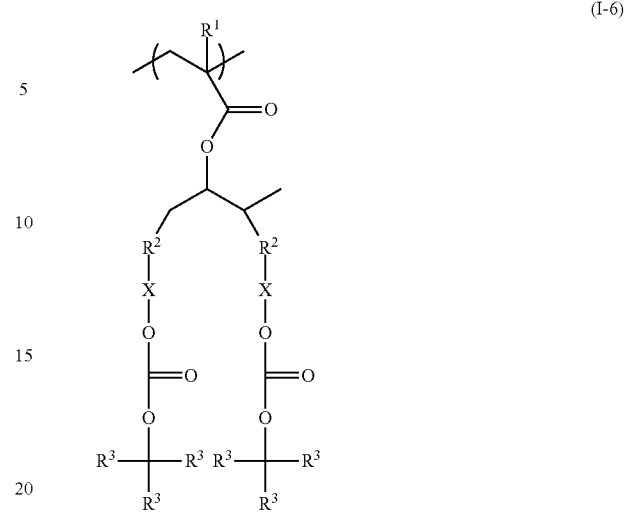

(I-6)

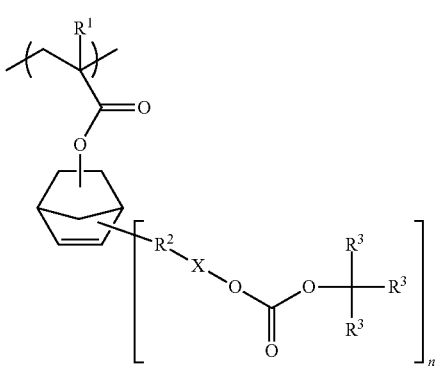

(I-4)

wherein $R^1$ represents a hydrogen atom, a methyl group, or a trifluoromethyl group, $R^2$ represents a single bond, a methylene group, an ethylene group, a 1-methylethylene group, a 2-methylethylene group, or a divalent alicyclic hydrocarbon group having 4 to 20 carbon atoms, provided that $R^2$ may be the same or different when a plurality of $R^2$ are present, $R^3$ individually represent a monovalent alicyclic hydrocarbon group having 4 to 20 carbon atoms or a linear or branched alkyl group having 1 to 4 carbon atoms, provided that two of $R^3$ may bond to form a divalent alicyclic hydrocarbon group having 4 to 20 carbon atoms together with the carbon atom bonded thereto, X represents a linear or branched fluoroalkylene group having 1 to 10 carbon atoms, provided that X may be the same or different when a plurality of X are present, and n is an integer from 1 to 5.

The repeating unit shown by the general formula (I) is preferably a repeating unit shown by the following general formula (Ia), and more preferably a repeating unit shown by the following general formula (I-2).

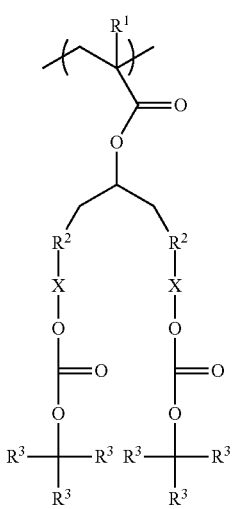

(I-5)

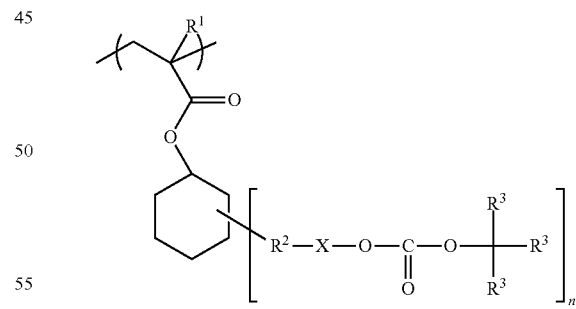

(Ia)

wherein $R^1$ represents a hydrogen atom, a methyl group, or a trifluoromethyl group, $R^2$ represents a single bond, a methylene group, an ethylene group, a 1-methylethylene group, a 2-methylethylene group, or a divalent alicyclic hydrocarbon group having 4 to 20 carbon atoms, provided that $R^2$ may be the same or different when a plurality of $R^2$ are present, $R^3$ individually represent a monovalent alicyclic hydrocarbon group having 4 to 20 carbon atoms or a linear or branched alkyl group having 1 to 4 carbon atoms, provided that two of $R^3$ may bond to form a divalent alicyclic hydrocarbon group having 4 to 20 carbon atoms together with the carbon atom bonded thereto, X represents a linear or branched fluoroalkylene group having 1 to 10 carbon atoms, provided that X may be the same or different when a plurality of X are present, and n is an integer from 1 to 5.

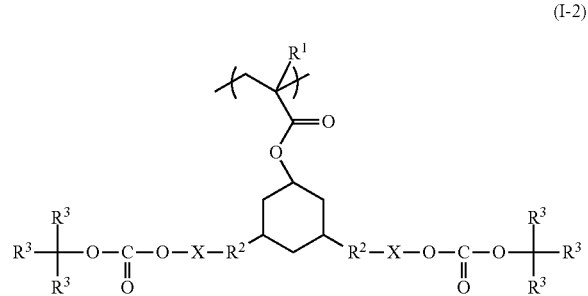

(I-2)

wherein $R^1$ represents a hydrogen atom, a methyl group, or a trifluoromethyl group, $R^2$ individually represent a single bond, a methylene group, an ethylene group, a 1-methylethylene group, a 2-methylethylene group, or a divalent alicyclic hydrocarbon group having 4 to 20 carbon atoms, $R^3$ individually represent a monovalent alicyclic hydrocarbon group having 4 to 20 carbon atoms or a linear or branched alkyl group having 1 to 4 carbon atoms, provided that two of $R^3$ may bond to form a divalent alicyclic hydrocarbon group having 4 to 20 carbon atoms together with the carbon atom bonded thereto, and X individually represent a linear or branched fluoroalkylene group having 1 to 10 carbon atoms.

The content of the repeating unit (I) in the fluorine-containing polymer is preferably 5 to 50 mol %, more preferably 10 to 40 mol %, and particularly preferably 15 to 30 mol %, based on the total amount (=100 mol %) of the repeating units included in the fluorine-containing polymer. If the content of the repeating unit (I) is less than 5 mol %, a sufficiently high receding contact angle may not be obtained. If the content of the repeating unit (I) exceeds 50 mol %, the pattern shape may deteriorate due to a decrease in solubility of the fluorine-containing polymer in a developer.

It is preferable that the fluorine-containing polymer according to one embodiment of the invention further include a repeating unit shown by the following general formula (2) (hereinafter may be referred to as "repeating unit (2)").

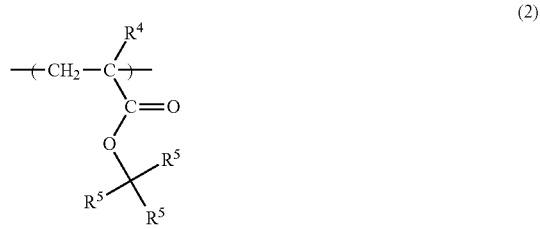

(2)

wherein $R^4$ represents a hydrogen atom, a methyl group, or a trifluoromethyl group, and $R^5$ individually represent a monovalent alicyclic hydrocarbon group having 4 to 20 carbon atoms or a linear or branched alkyl group having 1 to 4 carbon atoms, provided that two of $R^5$ may bond to form a divalent alicyclic hydrocarbon group having 4 to 20 carbon atoms together with the carbon atom bonded thereto.

Examples of the monovalent alicyclic hydrocarbon group having 4 to 20 carbon atoms represented by $R^5$ in the general formula (2) include groups including an alicyclic ring derived from a cycloalkane (e.g., norbornane, tricyclodecane, tetracyclododecane, adamantane, cyclobutane, cyclopentane, cyclohexane, cycloheptane, or cyclooctane), and the like. Note that $R^5$ may represent a group (derivative) obtained by substituting the alicyclic hydrocarbon group with at least one of a linear or branched alkyl group having 1 to 4 carbon atoms (e.g., methyl group, ethyl group, n-propyl group, i-propyl group, n-butyl group, 2-methylpropyl group, 1-methylpropyl group, or t-butyl group) and a cycloalkyl group.

Examples of the divalent alicyclic hydrocarbon group having 4 to 20 carbon atoms that is formed by two of $R^5$ in the general formula (2) together with the carbon atom bonded thereto (i.e., the carbon atom bonded to the oxygen atom) include cycloalkylene groups such as a cyclobutylene group, a cyclopentylene group, a cyclohexylene group, and a cyclooctylene group. Note that the divalent alicyclic hydrocarbon group may be a group (derivative) obtained by substituting a cycloalkylene group with at least one of a linear or branched alkyl group having 1 to 4 carbon atoms (e.g., methyl group, ethyl group, n-propyl group, i-propyl group, n-butyl group, 2-methylpropyl group, 1-methylpropyl group, or t-butyl group) and a cycloalkyl group.

Examples of the linear or branched alkyl group having 1 to 4 carbon atoms represented by $R^5$ in the general formula (2) include a methyl group, an ethyl group, an n-propyl group, an i-propyl group, an n-butyl group, a 2-methylpropyl group, a 1-methylpropyl group, a t-butyl group, and the like.

Preferable examples of —$C(R^5)_3$ in the general formula (2) include the groups mentioned above as preferable examples of —$C(R^3)_3$ in the general formula (1) (see the section entitled "I. Compound").

The fluorine-containing polymer according to one embodiment of the invention may include only one type of repeating unit (2), or may include two or more types of repeating unit (2).

The content of the repeating unit (2) in the fluorine-containing polymer is preferably 5 to 95 mol %, more preferably 30 to 90 mol %, and particularly preferably 50 to 85 mol %, based on the total amount (=100 mol %) of the repeating units included in the fluorine-containing polymer. If the content of the repeating unit (2) is within the above range, a sufficiently high receding contact angle and excellent lithographic performance can be implemented.

The fluorine-containing polymer according to one embodiment of the invention may further include an additional repeating unit other than the repeating units (I) and (2).

Examples of the additional repeating unit include (i) a repeating unit that includes a lactone skeleton, a hydroxyl group, a carboxyl group, or the like that improves the alkali solubility, (ii) a repeating unit that includes an aromatic hydrocarbon group that suppresses reflection from a substrate, (iii) a repeating unit that includes an aromatic hydrocarbon group or an alicyclic hydrocarbon group that improves the etching resistance, and the like. Among these, a repeating unit that includes a lactone skeleton and a repeating unit that includes an alicyclic hydrocarbon group are preferable.

Examples of a preferable compound that produces the repeating unit that includes a lactone skeleton (hereinafter may be referred to as "repeating unit (3)") include compounds shown by the following general formulas (3-1) to (3-6), and the like.

(3-1)

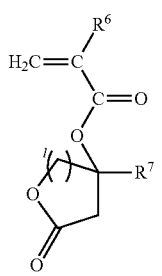

(3-2)

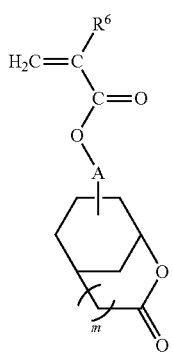

(3-3)

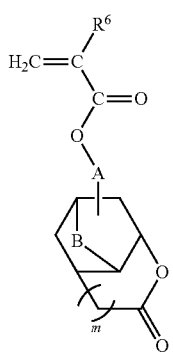

(3-4)

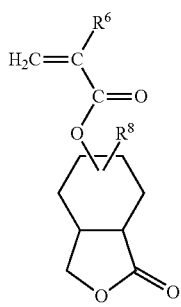

(3-5)

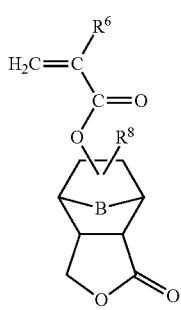

(3-6)

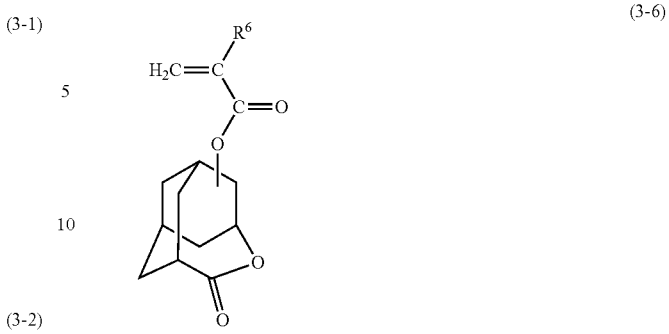

wherein $R^6$ represents a hydrogen atom or a methyl group, $R^7$ represents a hydrogen atom or a substituted or unsubstituted alkyl group having 1 to 4 carbon atoms, l is an integer from 0 to 3, $R^8$ represents a hydrogen atom or a methoxy group, A represents a single bond or a methylene group, m is 0 or 1, and B represents an oxygen atom or a methylene group.

Specific examples of the repeating unit that includes an alicyclic hydrocarbon group (hereinafter may be referred to as "repeating unit (4)") include a repeating unit shown by the following general formula (4).

(4)

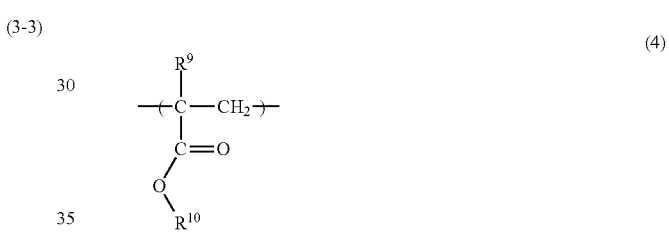

wherein $R^9$ represents a hydrogen atom, a methyl group, or a trifluoromethyl group, and $R^{10}$ represents an alicyclic hydrocarbon group having 4 to 20 carbon atoms.

Examples of the alicyclic hydrocarbon group having 4 to 20 carbon atoms represented by $R^{10}$ in the general formula (4) include hydrocarbon groups including an alicyclic ring derived from a cycloalkane such as cyclobutane, cyclopentane, cyclohexane, bicyclo[2.2.1]heptane, bicyclo[2.2.2]octane, tricyclo[5.2.1.0$^{2,6}$]decane, tetracyclo[6.2.1.1$^{3,6}$.0$^{2,7}$] dodecane, or tricycle[3.3.1.1$^{3,7}$]decane. Note that the alicyclic hydrocarbon group may be a group (derivative) obtained by substituting at least one hydrogen atom of the alicyclic hydrocarbon group with at least one of a linear or branched alkyl group having 1 to 4 carbon atoms (e.g., methyl group, ethyl group, n-propyl group, i-propyl group, n-butyl group, 2-methylpropyl group, 1-methylpropyl group, or t-butyl group), a cycloalkyl group, a hydroxyl group, a cyano group, a hydroxyalkyl group having 1 to 10 carbon atoms, a carboxyl group, an oxygen atom, and the like.

2. Production Method

The fluorine-containing polymer may be produced by polymerizing compounds that correspond to the above repeating units in an appropriate solvent optionally in the presence of a chain transfer agent using a radical initiator (e.g., hydroperoxide, dialkyl peroxide, diacyl peroxide, or azo compound).

Examples of the solvent used for polymerization include alkanes such as n-pentane, n-hexane, n-heptane, n-octane, n-nonane, and n-decane; cycloalkanes such as cyclohexane, cycloheptane, and cyclooctane; alicyclic hydrocarbons such as decalin and norbornane; aromatic hydrocarbons such as benzene, toluene, xylene, ethylbenzene, and cumene; halogenated hydrocarbons such as chlorobutanes, bromohexanes, dichloroethanes, hexamethylene dibromide, and chlorobenzene; saturated carboxylic acid esters such as ethyl acetate, n-butyl acetate, i-butyl acetate, and methyl propionate; ketones such as 2-butanone, 4-methyl-2-pentanone, and 2-heptanone; ethers such as tetrahydrofuran, dimethoxyethane, and diethoxyethane; alcohols such as methanol, ethanol, 1-propanol, 2-propanol, and 4-methyl-2-pentanol; and the like. These solvents may be used either individually or in combination.

The polymerization temperature is preferably 40 to 150° C., and more preferably 50 to 120° C. The polymerization (reaction) time is preferably 1 to 48 hours, and more preferably 1 to 24 hours.

3. Property Value

The polystyrene-reduced weight average molecular weight (hereinafter may be referred to as "Mw") of the fluorine-containing polymer determined by gel permeation chromatography (GPC) is preferably 1000 to 50,000, more preferably 1000 to 40,000, and particularly preferably 1000 to 30,000. If the Mw of the fluorine-containing polymer is less than 1000, a sufficiently high receding contact angle may not be obtained. If the Mw of the fluorine-containing polymer exceeds 50,000, the developability of the resulting resist may decrease.

The ratio (Mw/Mn) of the Mw to the polystyrene-reduced number average molecular weight (hereinafter may be referred to as "Mn") of the fluorine-containing polymer determined by GPC is preferably 1 to 5, and more preferably 1 to 4.

It is preferable that the content of impurities (e.g., halogen and metal) in the fluorine-containing polymer be as low as possible. If the fluorine-containing polymer has a low impurity content, the sensitivity, the resulting resist exhibits improved resolution, process stability, pattern shape, and the like. The fluorine-containing polymer may be purified by chemical purification (e.g., washing with water or liquid-liquid extraction), or a combination of chemical purification and physical purification (e.g., ultrafiltration or centrifugation), for example.

IV. Radiation-Sensitive Resin Composition

A radiation-sensitive resin composition according to one embodiment of the invention is described in detail below. The radiation-sensitive resin composition includes a polymer component including (A) the fluorine-containing polymer according to one embodiment of the invention (see the section entitled "III. Fluorine-containing polymer" (hereinafter may be referred to as "polymer (A)"), and (B) an acid-labile group-containing polymer (excluding the polymer (A)), and normally further includes a solvent.

Since the radiation-sensitive resin composition includes the polymer component including the polymer (A), the radiation-sensitive resin composition may suitably be used to form a resist film that is used for a resist pattern-forming method that includes liquid immersion lithography that applies radiation via an immersion liquid (e.g., water) that has a refractive index higher than that of air at a wavelength of 193 nm and is provided between a lens and the resist film. A resist film formed using the radiation-sensitive resin composition implements an excellent pattern shape, reduces the elution volume upon contact with the immersion liquid (e.g., water) during liquid immersion lithography, ensures that a high receding contact angle is formed by the resist film and the immersion liquid (e.g., water), and rarely undergoes development defects.

1. Polymer Component

The polymer component includes the acid-labile group-containing polymer (B) that differs from the polymer (A). The polymer (B) increases the receding contact angle, reduces the elution volume, and suppresses development defects, for example.

The radiation-sensitive resin composition may include the polymer (A) as a resist additive. The polymer (A) is preferably used in an amount of 0.1 to 40 parts by mass, and more preferably 0.5 to 35 parts by mass, based on 100 parts by mass of the polymer (B). If the amount of the polymer (A) is less than 0.1 parts by mass, the effects of the polymer (A) may not be obtained, so that the receding contact angle of the resulting resist film may decrease. If the amount of the polymer (A) exceeds 40 parts by mass, a rectangular resist pattern may not be obtained, or the depth of focus may decrease.

Acid-Labile Group-Containing Polymer (B)

The acid-labile group-containing polymer (B) is not particularly limited as long as the polymer (A) advantageously exerts its effects (i.e., an increase in receding contact angle, a decrease in elution volume, and suppression of development defects). The acid-labile group-containing polymer (B) is preferably a polymer that is insoluble or scarcely soluble in alkali, but becomes alkali-soluble due to an acid.

The expression "insoluble or scarcely soluble in alkali" means that a film that is formed only of the polymer (B) has a thickness equal to or more than 50% of the initial thickness when developed under alkaline development conditions employed when forming a resist pattern using a resist film that is formed of a radiation-sensitive resin composition that includes a polymer component including the polymer (B).

Examples of the polymer (B) include a polymer that includes an alicyclic skeleton such as a norbornane ring in the main chain and is obtained by polymerizing a norbornene derivative or the like, a polymer that includes a norbornane ring and a maleic anhydride derivative in the main chain and is obtained by copolymerizing a norbornene derivative and maleic anhydride, a polymer that includes a norbornane ring and a (meth)acrylic skeleton in the main chain and is obtained by copolymerizing a norbornene derivative and a (meth)acrylic compound, a polymer that includes a norbornane ring, a maleic anhydride derivative, and a (meth)acrylic skeleton in the main chain and is obtained by copolymerizing a norbornene derivative, maleic anhydride, and a (meth)acrylic compound, a polymer that includes a (meth)acrylic skeleton in the main chain and is obtained by copolymerizing (meth) acrylic compounds, and the like.

The polymer (B) is preferably a polymer that includes a (meth)acrylic skeleton in the main chain, and more preferably a polymer that includes at least one repeating unit (3) that includes a lactone skeleton (see the section entitled "III. Fluorine-containing polymer"). It is more preferable that the polymer (B) include at least one repeating unit (2) (see the section entitled "III. Fluorine-containing polymer") in addition to the repeating unit (3).

The content of the repeating unit (3) that includes a lactone skeleton in the polymer (B) is preferably 5 to 85 mol %, more preferably 10 to 70 mol %, and particularly preferably 15 to 60 mol %. If the content of the repeating unit (3) is less than 5 mol %, the developability and the exposure latitude may deteriorate. If the content of the repeating unit (3) exceeds 85 mol %, the solubility of the polymer (B) in a solvent and the resolution may deteriorate.

The content of the repeating unit (2) is preferably 10 to 70 mol %, more preferably 15 to 60 mol %, and particularly preferably 20 to 50 mol %. If the content of the repeating unit (2) is less than 10 mol %, the resolution of the resulting resist may decrease. If the content of the repeating unit (2) exceeds 70 mol %, the exposure latitude may deteriorate.

The copolymer (B) may be produced by the method described in the section entitled "2. Production method".

The Mw of the polymer (B) is not particularly limited, but is preferably 1000 to 100,000, more preferably 1000 to 30,000, and particularly preferably 1000 to 20,000. If the Mw of the polymer (B) is less than 1000, the heat resistance of the resulting resist may decrease. If the Mw of the polymer (B) exceeds 100,000, the developability of the resulting resist may decrease. The ratio (Mw/Mn) of the Mw to the Mn of the polymer (B) is preferably 1 to 5, and more preferably 1 to 3.

The content (solid content) of low-molecular-weight components derived from the compounds used to produce the polymer (B) is preferably 0.1 mass % or less, more preferably 0.07 mass % or less, and particularly preferably 0.05 mass % or less, based on 100 mass % of the polymer (B). If the content of low-molecular-weight components is 0.1 mass % or less, the elution volume upon contact with the immersion liquid (e.g., water) during liquid immersion lithography can be reduced. Moreover, it is possible to prevent production of foreign substances in the resist during storage, prevent uneven resist application, and sufficiently suppress occurrence of defects when forming a resist pattern.

Examples of the low-molecular-weight components derived from the compounds include components (e.g., monomer, dimer, trimer, and oligomer) having an Mw of 500 or less. Components having an Mw of 500 or less may be removed by chemical purification (e.g., washing with water or liquid-liquid extraction), or a combination of chemical purification and physical purification (e.g., ultrafiltration or centrifugation), for example. The content of low-molecular-weight components may be determined by high-performance liquid chromatography (HPLC).

It is preferable that the content of impurities (e.g., halogen and metal) in the polymer (B) be as low as possible. If the polymer (B) has a low impurity content, the resulting resist exhibits improved sensitivity, resolution, process stability, pattern shape, and the like. The polymer (B) may be purified by chemical purification (e.g., washing with water or liquid-liquid extraction), or a combination of chemical purification and physical purification (e.g., ultrafiltration or centrifugation), for example. The polymer component may include only one type of polymer (B), or may include two or more types of polymer (B).

2. Solvent

The radiation-sensitive resin composition is normally prepared as a composition solution by dissolving the components in a solvent so that the total solid content is 1 to 50 mass %, and preferably 1 to 25 mass %, and filtering the solution using a filter having a pore size of about 0.2 µm, for example.

Examples of the solvent include linear or branched ketones such as 2-butanone, 2-pentanone, 3-methyl-2-butanone, 2-hexanone, 4-methyl-2-pentanone, 3-methyl-2-pentanone, 3,3-dimethyl-2-butanone, 2-heptanone, 2-octanone; cyclic ketones such as cyclopentanone, 3-methylcyclopentanone, cyclohexanone, 2-methylcyclohexanone, 2,6-dimethylcyclohexanone, and isophorone; propylene glycol monoalkyl ether acetates such as propylene glycol monomethyl ether acetate, propylene glycol monoethyl ether acetate, propylene glycol mono-n-propyl ether acetate, propylene glycol mono-i-propyl ether acetate, propylene glycol mono-n-butyl ether acetate, propylene glycol mono-i-butyl ether acetate, propylene glycol mono-sec-butyl ether acetate, and propylene glycol mono-t-butyl ether acetate; alkyl 2-hydroxypropionates such as methyl 2-hydroxypropionate, ethyl 2-hydroxypropionate, n-propyl 2-hydroxypropionate, i-propyl 2-hydroxypropionate, n-butyl 2-hydroxypropionate, i-butyl 2-hydroxypropionate, sec-butyl 2-hydroxypropionate, and t-butyl 2-hydroxypropionate; alkyl 3-alkoxypropionates such as methyl 3-methoxypropionate, ethyl 3-methoxypropionate, methyl 3-ethoxypropionate, and ethyl 3-ethoxypropionate; n-propyl alcohol, i-propyl alcohol, n-butyl alcohol, t-butyl alcohol, cyclohexanol, ethylene glycol monomethyl ether, ethylene glycol monoethyl ether, ethylene glycol mono-n-propyl ether, ethylene glycol mono-n-butyl ether, diethylene glycol dimethyl ether, diethylene glycol diethyl ether, diethylene glycol di-n-propyl ether, diethylene glycol di-n-butyl ether, ethylene glycol monomethyl ether acetate, ethylene glycol monoethyl ether acetate, ethylene glycol mono-n-propyl ether acetate, propylene glycol monomethyl ether, propylene glycol monoethyl ether, propylene glycol mono-n-propyl ether, toluene, xylene, ethyl 2-hydroxy-2-methylpropionate, ethoxyethyl acetate, ethyl hydroxyacetate, methyl 2-hydroxy-3-methylbutyrate, 3-methoxybutylacetate, 3-methyl-3-methoxybutylacetate, 3-methyl-3-methoxybutylpropionate, 3-methyl-3-methoxybutylbutyrate, ethyl acetate, n-propyl acetate, n-butyl acetate, methyl acetoacetate, ethyl acetoacetate, methyl pyruvate, ethyl pyruvate, N-methylpyrrolidone, N,N-dimethylformamide, N,N-dimethylacetamide, benzyl ethyl ether, di-n-hexyl ether, diethylene glycol monomethyl ether, diethylene glycol monoethyl ether, caproic acid, caprylic acid, 1-octanol, 1-nonanol, benzyl alcohol, benzyl acetate, ethyl benzoate, diethyl oxalate, diethyl maleate, γ-butyrolactone, ethylene carbonate, propylene carbonate, and the like.

Among these, linear or branched ketones, cyclic ketones, propylene glycol monoalkyl ether acetates, alkyl 2-hydroxypropionates, alkyl 3-alkoxypropionates, γ-butyrolactone, and the like are preferable. These solvents may be used either individually or in combination.

3. Photoacid Generator

The radiation-sensitive resin composition according to one embodiment of the invention preferably further includes a photoacid generator (hereinafter may be referred to as "acid generator (C)") in addition to the polymer component including the polymer (A) and the polymer (B) and the solvent. The radiation-sensitive resin composition may include only one type of acid generator (C), or may include two or more types of acid generator (C).

The acid generator (C) generates an acid upon exposure. The acid-dissociable group or the acid-labile group included in the polymer component (polymers (A) and (B)) dissociates (i.e., the protecting group is eliminated) due to the acid generated by the acid generator (C), so that the exposed area of the resist film becomes readily soluble in an alkaline developer to obtain a positive-tone resist pattern.

The acid generator (C) preferably includes a compound shown by the following general formula (5).

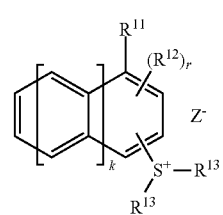

(5)

wherein $R^{11}$ represents a hydrogen atom, a fluorine atom, a hydroxyl group, a linear or branched alkyl group having 1 to 10 carbon atoms, a linear or branched alkoxy group having 1 to 10 carbon atoms, or a linear or branched alkoxycarbonyl group having 2 to 11 carbon atoms, $R^{12}$ represents a linear or branched alkyl group having 1 to 10 carbon atoms, a linear or branched alkoxy group having 1 to 10 carbon atoms, or a linear, branched, or cyclic alkanesulfonyl group having 1 to 10 carbon atoms, $R^{13}$ individually represent a linear or branched alkyl group having 1 to 10 carbon atoms, a substituted or unsubstituted phenyl group, or a substituted or unsubstituted naphthyl group, provided that $R^{13}$ may bond to form a substituted or unsubstituted divalent group having 2 to 10 carbon atoms, k is an integer from 0 to 2, $Z^-$ represents an anion shown by the following general formula (6), and r is an integer from 0 to 10.

$$R^{14}C_qF_{2q}SO_3^- \quad (6)$$

wherein $R^{14}$ represents a fluorine atom or a hydrocarbon group having 1 to 12 carbon atoms, and q is an integer from 1 to 10.

Examples of the linear or the branched alkyl group having 1 to 10 carbon atoms represented by $R^{11}$, $R^{12}$, and $R^{13}$ in the general formula (5) include a methyl group, an ethyl group, an n-propyl group, an i-propyl group, an n-butyl group, a 2-methylpropyl group, a 1-methylpropyl group, a t-butyl group, an n-pentyl group, a neopentyl group, an n-hexyl group, an n-heptyl group, an n-octyl group, a 2-ethylhexyl group, an n-nonyl group, an n-decyl group, and the like. Among these, a methyl group, an ethyl group, an n-butyl group, and a t-butyl group are preferable.

Examples of the linear or branched alkoxy group having 1 to 10 carbon atoms represented by $R^{11}$ and $R^{12}$ in the general formula (5) include a methoxy group, an ethoxy group, an n-propoxy group, an i-propoxy group, an n-butoxy group, a 2-methylpropoxy group, a 1-methylpropoxy group, a t-butoxy group, an n-pentyloxy group, a neopentyloxy group, an n-hexyloxy group, an n-heptyloxy group, an n-octyloxy group, a 2-ethylhexyloxy group, an n-nonyloxy group, an n-decyloxy group, and the like. Among these, a methoxy group, an ethoxy group, an n-propoxy group, and an n-butoxy group are preferable.

Examples of the linear or branched alkoxycarbonyl group having 2 to 11 carbon atoms represented by $R^{11}$ in the general formula (5) include a methoxycarbonyl group, an ethoxycarbonyl group, an n-propoxycarbonyl group, an i-propoxycarbonyl group, an n-butoxycarbonyl group, a 2-methylpropoxycarbonyl group, a 1-methylpropoxycarbonyl group, a t-butoxycarbonyl group, an n-pentyloxycarbonyl group, a neopentyloxycarbonyl group, an n-hexyloxycarbonyl group, an n-heptyloxycarbonyl group, an n-octyloxycarbonyl group, a 2-ethylhexyloxycarbonyl group, an n-nonyloxycarbonyl group, an n-decyloxycarbonyl group, and the like. Among these, a methoxycarbonyl group, an ethoxycarbonyl group, and an n-butoxycarbonyl group are preferable.

Examples of the linear, branched, or cyclic alkanesulfonyl group having 1 to 10 carbon atoms represented by $R^{12}$ in the general formula (5) include a methanesulfonyl group, an ethanesulfonyl group, an n-propanesulfonyl group, an n-butanesulfonyl group, a tert-butanesulfonyl group, an n-pentanesulfonyl group, a neopentanesulfonyl group, an n-hexanesulfonyl group, an n-heptanesulfonyl group, an n-octanesulfonyl group, a 2-ethylhexanesulfonyl group, an n-nonanesulfonyl group, an n-decanesulfonyl group, a cyclopentanesulfonyl group, a cyclohexanesulfonyl group, and the like. Among these, a methanesulfonyl group, an ethanesulfonyl group, an n-propanesulfonyl group, an n-butanesulfonyl group, a cyclopentanesulfonyl group, and a cyclohexanesulfonyl group are preferable.

r in the general formula (5) is preferably an integer from 0 to 2.

Examples of the substituted or unsubstituted phenyl group represented by $R^{13}$ in the general formula (5) include a phenyl group; phenyl groups substituted with a linear or branched alkyl group having 1 to 10 carbon atoms or a cycloalkyl group, such as an o-tolyl group, an m-tolyl group, a p-tolyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 2,4,6-trimethylphenyl group, a 4-ethylphenyl group, a 4-t-butylphenyl group, 4-cyclohexylphenyl group, and a 4-fluorophenyl group; groups obtained by substituting a phenyl group or the alkyl-substituted phenyl group with at least one group selected from a hydroxyl group, a carboxyl group, a cyano group, a nitro group, an alkoxy group, an alkoxyalkyl group, an alkoxycarbonyl group, an alkoxycarbonyloxy group, and the like.

Examples of the alkoxy group as a substituent for a phenyl group or the alkyl-substituted phenyl group include linear, branched, or cyclic alkoxy groups having 1 to 20 carbon atoms, such as a methoxy group, an ethoxy group, an n-propoxy group, an i-propoxy group, an n-butoxy group, a 2-methylpropoxy group, a 1-methylpropoxy group, a t-butoxy group, a cyclopentyloxy group, and a cyclohexyloxy group, and the like.

Examples of the alkoxyalkyl group include linear, branched, or cyclic alkoxyalkyl groups having 2 to 21 carbon atoms, such as a methoxymethyl group, an ethoxymethyl group, a 1-methoxyethyl group, a 2-methoxyethyl group, a 1-ethoxyethyl group, and a 2-ethoxyethyl group, and the like.

Examples of the alkoxycarbonyl group include linear, branched, or cyclic alkoxycarbonyl groups having 2 to 21 carbon atoms, such as a methoxycarbonyl group, an ethoxycarbonyl group, an n-propoxycarbonyl group, an i-propoxycarbonyl group, an n-butoxycarbonyl group, a 2-methylpropoxycarbonyl group, a 1-methylpropoxycarbonyl group, a t-butoxycarbonyl group, a cyclopentyloxycarbonyl group, and a cyclohexyloxycarbonyl group, and the like.

Examples of the alkoxycarbonyloxy group include linear, branched, or cyclic alkoxycarbonyloxy groups having 2 to 21 carbon atoms, such as a methoxycarbonyloxy group, an ethoxycarbonyloxy group, an n-propoxycarbonyloxy group, an i-propoxycarbonyloxy group, an n-butoxycarbonyloxy group, a t-butoxycarbonyloxy group, and a cyclopentyloxycarbonyloxy group, a cyclohexyloxycarbonyloxy group, and the like.

Among these, a phenyl group, a 4-cyclohexylphenyl group, a 4-t-butylphenyl group, a 4-methoxyphenyl group, a 4-t-butoxyphenyl group, and the like are preferable.

Examples of the substituted or unsubstituted naphthyl group represented by $R^{13}$ in the general formula (5) include naphthyl groups substituted or unsubstituted with a linear or branched alkyl group having 1 to 10 carbon atoms or a cycloalkyl group, such as a 1-naphthyl group, a 2-methyl-1-naphthyl group, a 3-methyl-1-naphthyl group, a 4-methyl-1-naphthyl group, a 5-methyl-1-naphthyl group, a 6-methyl-1-naphthyl group, a 7-methyl-1-naphthyl group, a 8-methyl-1-naphthyl group, a 2,3-dimethyl-1-naphthyl group, a 2,4-dimethyl-1-naphthyl group, a 2,5-dimethyl-1-naphthyl group, a 2,6-dimethyl-1-naphthyl group, a 2,7-dimethyl-1-naphthyl group, a 2,8-dimethyl-1-naphthyl group, a 3,4-dimethyl-1-naphthyl group, a 3,5-dimethyl-1-naphthyl group, a 3,6-dimethyl-1-naphthyl group, a 3,7-dimethyl-1-naphthyl group, a 3,8-dimethyl-1-naphthyl group, a 4,5-dimethyl-1-naphthyl group, a 5,8-dimethyl-1-naphthyl group, a 4-ethyl-1-naphthyl group, a 2-naphthyl group, a 1-methyl-2-naphthyl group, a 3-methyl-2-naphthyl group, and a 4-methyl-2-naphthyl group; groups obtained by substituting a naphthyl group or the alkyl-substituted naphthyl group with at least one group such as a hydroxyl group, a carboxyl group, a cyano group, a nitro group, an alkoxyl group, an alkoxyalkyl group, an alkoxycarbonyl group, or an alkoxycarbonyloxy group; and the like.

Examples of the alkoxyl group, the alkoxyalkyl group, the alkoxycarbonyl group, and the alkoxycarbonyloxy group as a substituent for a naphthyl group or the alkyl-substituted naphthyl group include the alkoxyl groups, the alkoxyalkyl groups, the alkoxycarbonyl groups, and the alkoxycarbonyloxy groups mentioned above in connection with a phenyl group and the alkyl-substituted phenyl group.

Among these, a 1-naphthyl group, a 1-(4-methoxynaphthyl) group, a 1-(4-ethoxynaphthyl) group, a 1-(4-n-propoxynaphthyl) group, a 1-(4-n-butoxynaphthyl) group, a 2-(7-methoxynaphthyl) group, a 2-(7-ethoxynaphthyl) group, a 2-(7-n-propoxynaphthyl) group, a 2-(7-n-butoxynaphthyl) group, and the like are preferable.

The divalent group having 2 to 10 carbon atoms formed by $R^{13}$ in the general formula (5) is preferably a group that forms a 5 or 6-membered ring (more preferably a 5-membered ring (i.e., tetrahydrothiophene ring)) together with the sulfur cation in the general formula (5). Examples of a substituent for the divalent group include the groups (e.g., hydroxyl group, carboxyl group, cyano group, nitro group, alkoxy group, alkoxyalkyl group, alkoxycarbonyl group, and alkoxycarbonyloxy group) mentioned above in connection with a phenyl group and the alkyl-substituted phenyl group.

It is preferable that $R^{13}$ in the general formula (5) be a methyl group, an ethyl group, a phenyl group, a 4-methoxyphenyl group, or a 1-naphthyl group, or bond to form a divalent group that forms a tetrahydrothiophene ring structure together with the sulfur cation.

The $C_qF_{2q}$ group in the anion moiety (general formula (6)) represented by $Z^-$ in the general formula (5) is a linear or branched perfluoroalkylene group having q carbon atoms. q in the general formula (6) is preferably 1, 2, 4, or 8.

The substituted or unsubstituted hydrocarbon group having 1 to 12 carbon atoms represented by $R^{14}$ in the general formula (6) is preferably an alkyl group having 1 to 12 carbon atoms, a cycloalkyl group, or a bridged alicyclic hydrocarbon group. Specific examples of the substituted or unsubstituted hydrocarbon group having 1 to 12 carbon atoms include a methyl group, an ethyl group, an n-propyl group, an i-propyl group, an n-butyl group, a 2-methylpropyl group, a 1-methylpropyl group, a t-butyl group, an n-pentyl group, an neopentyl group, an n-hexyl group, a cyclohexyl group, an n-heptyl group, an n-octyl group, a 2-ethylhexyl group, an n-nonyl group, an n-decyl group, a norbornyl group, a norbornylmethyl group, a hydroxynorbornyl group, an adamantyl group, and the like.

Specific examples of a preferable compound shown by the general formula (5) include triphenylsulfonium trifluoromethanesulfonate, tri-tert-butylphenylsulfonium trifluoromethanesulfonate, 4-cyclohexylphenyl-diphenylsulfonium trifluoromethanesulfonate, 4-methanesulfonylphenyl-diphenylsulfonium trifluoromethanesulfonate, 1-(3,5-dimethyl 4-hydroxyphenyl)tetrahydrothiophenium trifluoromethanesulfonate, 1-(4-n-butoxynaphthyl)tetrahydrothiophenium trifluoromethanesulfonate, triphenylsulfonium perfluoro-n-butanesulfonate, tri-tert-butylphenylsulfonium perfluoro-n-butanesulfonate, 4-cyclohexylphenyl-diphenylsulfonium perfluoro-n-butanesulfonate, 4-methanesulfonylphenyl-diphenylsulfonium perfluoro-n-butanesulfonate, 1-(3,5-dimethyl-4-hydroxyphenyl)tetrahydrothiophenium perfluoro-n-butanesulfonate, 1-(4-n-butoxynaphthyl)tetrahydrothiophenium perfluoro-n-butanesulfonate, triphenylsulfonium perfluoro-n-octanesulfonate, tri-tert-butylphenylsulfonium perfluoro-n-octanesulfonate, 4-cyclohexylphenyl-diphenylsulfonium perfluoro-n-octanesulfonate, 4-methanesulfonylphenyl-diphenylsulfonium perfluoro-n-octanesulfonate, 1-(3,5-dimethyl-4-hydroxyphenyl)tetrahydrothiophenium perfluoro-n-octanesulfonate, 1-(4-n-butoxynaphthyl)tetrahydrothiophenium perfluoro-n-octanesulfonate, triphenylsulfonium 2-(bicyclo[2.2.1]hept-2'-yl)-1,1,2,2-tetrafluoroethanesulfonate, tri-tert-butylphenylsulfonium 2-(bicyclo[2.2.1]hept-2'-yl)-1,1,2,2-tetrafluoroethanesulfonate, 4-cyclohexylphenyldiphenylsulfonium 2-(bicyclo[2.2.1]hept-2'-yl)-1,1,2,2-tetrafluoroethane sulfonate, 4-methanesulfonylphenyldiphenylsulfonium 2-(bicyclo[2.2.1]hept-2'-yl)-1,1,2,2-tetrafluoroethanesulfonate, 1-(3,5-dimethyl-4-hydroxyphenyl)tetrahydrothiophenium 2-(bicyclo[2.2.1]hept-2'-yl)-1,1,2,2-tetrafluoroethanesulfonate, 1-(4-n-butoxynaphthyl)tetrahydrothiophenium 2-(bicyclo[2.2.1]hept-2'-yl)-1,1,2,2-tetrafluoroethanesulfonate, triphenylsulfonium 2-(bicyclo[2.2.1]hept-2'-yl)-1,1-difluoroethanesulfonate, tri-tert-butylphenylsulfonium 2-(bicyclo[2.2.1]hept-2'-yl)-1,1-difluoroethanesulfonate, 4-cyclohexylphenyldiphenylsulfonium 2-(bicyclo[2.2.1]hept-2'-yl)-1,1-difluoroethanesulfonate, 4-methanesulfonylphenyldiphenylsulfonium 2-(bicyclo[2.2.1]hept-2'-yl)-1,1-difluoroethanesulfonate, 1-(3,5-dimethyl-4-hydroxyphenyl)tetrahydrothiophenium 2-(bicyclo[2.2.1]hept-2'-yl)-1,1-difluoroethanesulfonate, 1-(4-n-butoxynaphthyl)tetrahydrothiophenium 2-(bicyclo[2.2.1]hept-2'-yl)-1,1-difluoroethanesulfonate, and the like.

4. Nitrogen-Containing Compound

The radiation-sensitive resin composition may further include a nitrogen-containing compound (hereinafter may be referred to as "nitrogen-containing compound (E)") as an additive.

The nitrogen-containing compound (E) controls diffusion of an acid generated from the acid generator upon exposure within the resist film, and suppresses undesired chemical reactions in the unexposed area. The acid diffusion controller improves the storage stability of the resulting radiation-sensitive resin composition. Moreover, the acid diffusion controller further improves the resolution of the resulting resist and suppresses a change in the line width of the resist pattern due to a variation in post-exposure delay (PED) from exposure to post-exposure bake, so that a radiation-sensitive resin composition that exhibits remarkably superior process stability can be obtained.

Examples of the nitrogen-containing compound (E) include tertiary amine compounds, other amine compounds, amide group-containing compounds, urea compounds, nitrogen-containing heterocyclic compounds, and the like. The radiation-sensitive resin composition may include only one type of nitrogen-containing compound (E), or may include two or more types of nitrogen-containing compound (E).

The nitrogen-containing compound (E) is preferably used in an amount of 15 parts by mass or less, more preferably 10 parts by mass or less, and particularly preferably 5 parts by mass or less, based on 100 parts by mass of the polymer component. If the amount of the nitrogen-containing compound (E) exceeds 15 parts by mass, the sensitivity of the resulting resist may decrease. Note that the pattern shape or the dimensional accuracy of the resulting resist may decrease depending on the processing conditions if the amount of the nitrogen-containing compound (E) is less than 0.001 parts by mass.

5. Other Additives

The radiation-sensitive resin composition may optionally include other additives such as an aliphatic additive, a surfactant, and a sensitizer.

The alicyclic additive further improves the dry etching resistance, the pattern shape, adhesion to a substrate, and the like.

Specific examples of the alicyclic additive include adamantane derivatives such as 1-adamantanecarboxylic acid, 2-adamantanone, t-butyl-1-adamantanecarboxylate, t-butoxycarbonylmethyl 1-adamantanecarboxylate, α-butyrolactone 1-adamantanecarboxylate, di-t-butyl 1,3-adamantanedicarboxylate, t-butyl 1-adamantaneacetate, t-butoxycarbonylmethyl 1-adamantaneacetate, di-t-butyl 1,3-adamantanediacetate, and 2,5-dimethyl-2,5-di(adamantylcarbonyloxy)hexane; deoxycholates such as t-butyl deoxycholate, t-butoxycarbonylmethyl deoxycholate, 2-ethoxyethyl deoxycholate, 2-cyclohexyloxyethyl deoxycholate, 3-oxocyclohexyl deoxycholate, tetrahydropyranyl deoxycholate, and mevalonolactone deoxycholate; lithocholates such as t-butyl lithocholate, t-butoxycarbonylmethyl lithocholate, 2-ethoxyethyl lithocholate, 2-cyclohexyloxyethyl lithocholate, 3-oxocyclohexyl lithocholate, tetrahydropyranyl lithocholate, and mevalonolactone lithocholate; 3-(2-hydroxy-2,2-bis(trifluoromethyl)ethyl)tetracyclo[$6.2.1.1^{3,6}.0^{2,7}$]dodecane; and the like. These alicyclic additives may be used either individually or in combination.

The surfactant improves the applicability, striation, developability, and the like.

Examples of the surfactant include nonionic surfactants such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate, and polyethylene glycol distearate, commercially available products such as KP341 (manufactured by Shin-Etsu Chemical Co., Ltd.), Polyflow No. 75, Polyflow No. 95 (manufactured by Kyoeisha Chemical Co., Ltd.), EFTOP EF301, EFTOP EF303, EFTOP EF352 (manufactured by JEMCO, Inc.), Megafac F171, Megafac F173 (manufactured by DIC Corporation), Fluorad FC430, Fluorad FC431 (manufactured by Sumitomo 3M Ltd.), Asahi Guard AG710, Surflon S-382, Surflon SC-101, Surflon SC-102, Surflon SC-103, Surflon SC-104, Surflon SC-105, Surflon SC-106 (manufactured by Asahi Glass Co., Ltd.), and the like. These surfactants may be used either individually or in combination.

The sensitizer absorbs the energy of radiation, and transmits the energy to the acid generator (C) so that the amount of acid generated by the acid generator (C) increases. Specifically, the sensitizer improves the apparent sensitivity of the radiation-sensitive resin composition.

Examples of the sensitizer include carbazoles, acetophenones, benzophenones, naphthalenes, phenols, biacetyl, eosine, rose bengal, pyrenes, anthracenes, phenothiazines, and the like. These sensitizers may be used either individually or in combination.

A dye or a pigment visualizes the latent image in the exposed area, and reduces the effects of halation during exposure. An adhesion improver improves adhesion to a substrate. Examples of other additives include an alkali-soluble resin, a low-molecular-weight alkali-solubility controller that includes an acid-dissociable protecting group, a halation inhibitor, a preservation stabilizer, an antifoaming agent, and the like.

V. Resist Pattern-Forming Method

The radiation-sensitive resin composition may be useful as a chemically-amplified resist. When using the radiation-sensitive resin composition as a chemically-amplified resist, the acid-dissociable group or the acid-labile group included in the polymer component dissociates due to an acid generated by the acid generator upon exposure so that a carboxyl group is produced. As a result, the solubility of the exposed area of the resist in an alkaline developer increases. Therefore, the exposed area is dissolved (removed) in an alkaline developer to obtain a positive-tone resist pattern.

When forming a resist pattern using the radiation-sensitive resin composition, the composition solution is applied to a substrate (e.g., silicon wafer or aluminum-coated wafer) by an appropriate application method (e.g., rotational coating, cast coating, or roll coating) to form a resist film. The resist film is optionally pre-baked (PB), and exposed to form a given resist pattern.

Radiation used for exposure may be appropriately selected from visible rays, ultraviolet rays, deep ultraviolet rays, X-rays, charged particle rays, and the like depending on the type of the acid generator (C). It is preferable to use deep ultraviolet rays such as ArF excimer laser light (wavelength: 193 nm) or KrF excimer laser light (wavelength: 248 nm). It is particularly preferable to use ArF excimer laser light (wavelength: 193 nm).

The exposure conditions (e.g., dose) may be appropriately selected depending on the composition of the radiation-sensitive resin composition, the type of additive, and the like. A liquid refractive medium (immersion liquid) (e.g., purified water or fluorine-containing inert liquid) having a given thickness is interposed (at least over the resist film) between the lens and the resist film formed on the substrate during exposure. It is preferable to perform post-exposure bake (PEB) after exposure. PEB ensures smooth dissociation of the acid-dissociable group or the acid-labile group included in the polymer component. The PEB temperature is determined depending on the composition of the radiation-sensitive resin composition, but is preferably 30 to 200° C., and more preferably 50 to 170° C.

In order to bring out the potential of the radiation-sensitive resin composition to a maximum extent, an organic or inorganic antireflective film may be formed on a substrate, as disclosed in Japanese Examined Patent Publication (KOKOKU) No. 6-12452 (Japanese Patent Application Publication (KOKAI) No. 59-93448), for example. A protective film may be formed on the resist film so that the resist film is not affected by basic impurities and the like contained in the environmental atmosphere, as disclosed in Japanese Patent Application Publication (KOKAI) No. 5-188598, for example. In order to prevent outflow of the acid generator (C) and the like from the resist film during liquid immersion lithography, a liquid immersion lithography protective film may be formed on the resist film, as disclosed in Japanese Patent Application Publication (KOKAI) No. 2005-352384, for example. These methods may be used in combination.

The exposed resist film is developed using a developer to form a given resist pattern.

An alkaline aqueous solution prepared by dissolving at least one alkaline compound (e.g., sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide, pyrrole, piperidine, choline, 1,8-diazabicyclo-[5.4.0]-7-undecene, and 1,5-diazabicyclo-[4.3.0]-5-nonene) in water is preferable as the developer used for development. The concentration of the alkaline aqueous solution is normally 10 mass % or less. If the concentration of the alkaline aqueous solution exceeds 10 mass %, the unexposed area may also be dissolved in the developer.

An organic solvent may be added to the alkaline aqueous solution. Examples of the organic solvent include ketones such as acetone, methyl ethyl ketone, methyl i-butyl ketone, cyclopentanone, cyclohexanone, 3-methylcyclopentanone, and 2,6-dimethylcyclohexanone; alcohols such as methanol, ethanol, n-propyl alcohol, i-propyl alcohol, n-butyl alcohol, t-butyl alcohol, cyclopentanol, cyclohexanol, 1,4-hexanediol, and 1,4-hexanedimethylol; ethers such as tetrahydrofuran and dioxane; esters such as ethyl acetate, n-butyl acetate, and i-amyl acetate; aromatic hydrocarbons such as toluene and xylene; phenol, acetonylacetone, dimethylformamide; and the like. These organic solvents may be used either individually or in combination.

The organic solvent is preferably used in an amount of 100 vol % or less based on the amount of the alkaline aqueous solution. If the amount of the organic solvent exceeds 100 vol %, the exposed area may remain undeveloped due to a decrease in developability. An appropriate amount of surfactant or the like may be added to the alkaline aqueous solution. The resist film is normally washed with water, and dried after development using the developer.

EXAMPLES

The invention is further described below by way of examples. Note that the invention is not limited to the following examples. In the examples and comparative examples, the unit "parts" refers to "parts by mass", and the unit "%" refers to "mass %", unless otherwise specified. The property measuring methods and the property evaluation methods employed in the examples and comparative examples are described below.

Weight Average Molecular Weight (Mw) and Number Average Molecular Weight (Mn)

The weight average molecular weight (Mw) and the number average molecular weight (Mn) of the polymer were determined by gel permeation chromatography (GPC) (standard: monodispersed polystyrene) using GPC columns manufactured by Tosoh Corp. (G2000HXL×2, G3000HXL× 1, G4000HXL×1) under the following conditions. The dispersity (Mw/Mn) was calculated from the measurement results.

Flow rate: 1.0 ml/min
Eluant: tetrahydrofuran
Column temperature: 40° C.
$^{13}$C-NMR Analysis The polymer was subjected to $^{13}$C-NMR analysis using a mass spectrometer "JNM-EX270" (manufactured by JEOL Ltd.).

Example 1

Synthesis of Compound (M-4)

A three-necked flask (200 ml) equipped with a reflux cooling tube and a dropping funnel was charged with 42.03 g (60 mmol) of the compound shown by the following formula (a-1) (hereinafter may be referred to as "compound (a-1)"), 1.52 g (15 mmol) of triethylamine (NEt$_3$), 1.83 g (15 mmol) of dimethylaminopyridine (DMAP), and 80 ml of tetrahydrofuran (THF). The mixture was heated (refluxed) at 70° C. using an oil bath. A solution prepared by dissolving 39.28 g (180 mmol) of the compound shown by the following formula (a-5) in 20 ml of THF was added dropwise to the mixture over 5 minutes. The reaction was tracked by thin-layer chromatography (TLC), and terminated when the compound (a-1) had disappeared. The mixture was then allowed to cool to room temperature. After the addition of 40 ml of water and 75 ml of ethyl acetate, the organic layer was removed by a liquid separation operation. The organic layer was concentrated using a rotary evaporator, and subjected to silica gel column chromatography ("Wakogel C-300" manufactured by Wako Pure Chemical Industries, Ltd.) using an eluant (hexane/ethyl acetate=2/1) to isolate the target compound shown by the following formula (M-4) (hereinafter may be referred to as "compound (M-4)") (colorless liquid) (yield: 80%).

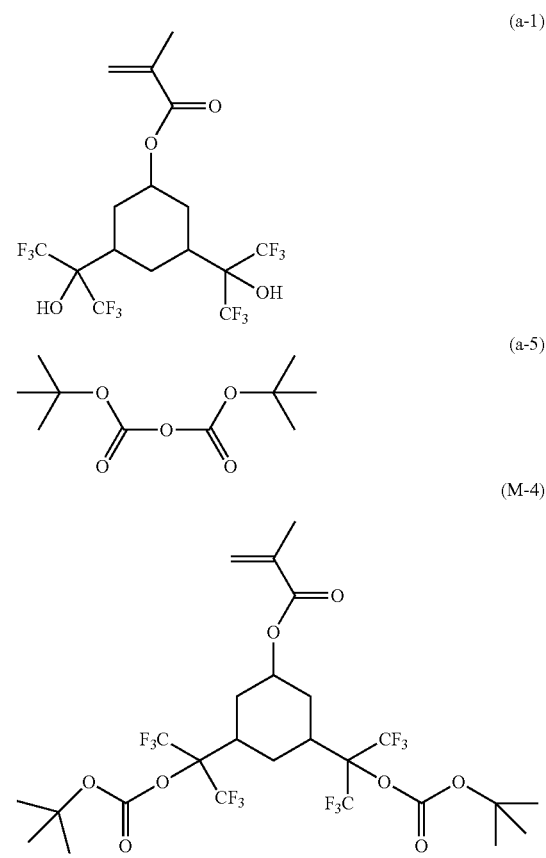

The structure of the compound (M-4) was determined by $^1$H-NMR. The results of the $^1$H-NMR analysis are given below. Note that the $^1$H-NMR analysis was performed in the same manner as the $^{13}$C-NMR analysis.

$^1$H-NMR (400 MHz, CDCl$_3$): δ(ppm)=6.10 (d, 1H), 5.66 (d, 1H), 4.82-4.95 (m, 1H), 3.30 (t, 2H), 2.20-2.25 (m, 2H), 1.91 (s, 3H), 1.73-1.80 (m, 4H), 1.48 (s, 18H)

Examples 2 to 4

Synthesis of Compounds (M-5) to (M-7)

Compounds (M-5) to (M-7) were synthesized in the same manner as in Example 1, except for using each compound ((a-2) to (a-4)) shown in Table 1 instead of the compound (a-1). The type and the yield of the resulting compound are also shown in Table 1.

TABLE 1

|  | Raw material | Product | |
|---|---|---|---|
|  | Type | Yield (%) | Type |
| Example 1 | (a-1) | 80 | (M-4) |
| Example 2 | (a-2) | 75 | (M-5) |
| Example 3 | (a-3) | 74 | (M-6) |
| Example 4 | (a-4) | 77 | (M-7) |

The raw material and the product shown in Table 1, and the results of the $^1$H-NMR analysis are given below.

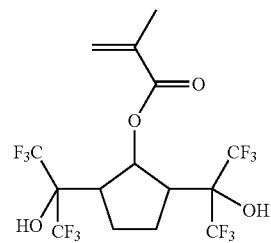
(a-2)

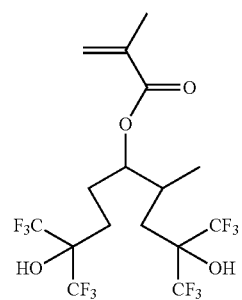
(a-3)

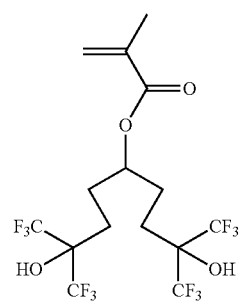
(a-4)

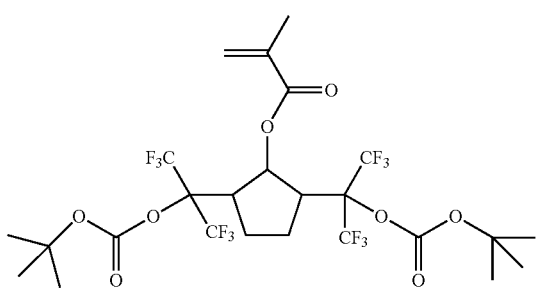
(M-5)

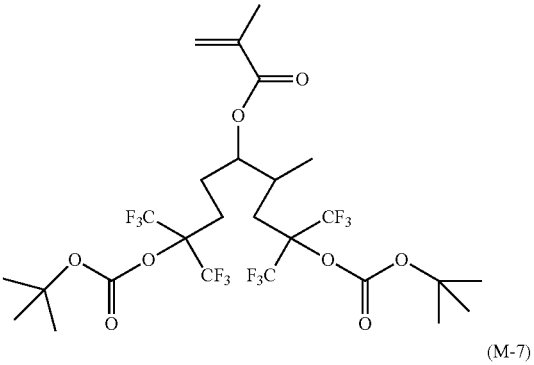
(M-6)

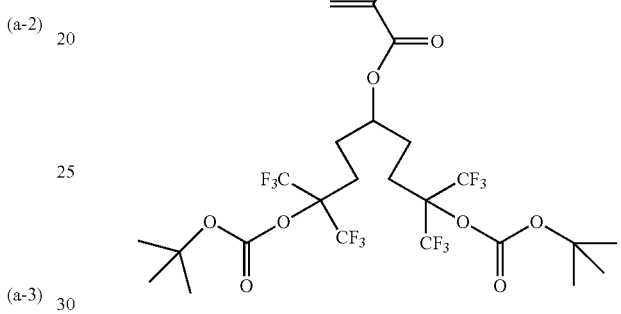
(M-7)

Compound (M-5)
$^1$H-NMR (400 MHz, CDCl$_3$): δ(ppm)=6.13 (d, 1H), 5.64 (d, 1H), 4.84-4.97 (m, 1H), 2.54-2.80 (m, 2H), 2.11 (s, 3H), 1.95-1.65 (m, 4H), 1.45 (s, 18H)

Compound (M-6)
$^1$H-NMR (400 MHz, CDCl$_3$): δ(ppm)=6.12 (d, 1H), 5.62 (d, 1H), 4.77-4.92 (m, 1H), 2.43-2.61 (m, 1H), 2.13 (s, 3H), 1.75 (q, 2H), 1.66 (t, 2H), 1.55 (d, 2H), 1.38 (s, 18H), 1.10 (d, 3H)

Compound (M-7)
$^1$H-NMR (400 MHz, CDCl$_3$): δ(ppm)=6.13 (d, 1H), 5.63 (d, 1H), 4.76-4.88 (m, 1H), 2.14 (s, 3H), 1.83 (td, 4H), 1.62 (t, 4H), 1.38 (s, 18H)

Example 5

Production of Fluorine-Containing Polymer (A-1)

14.96 g (90 mol %) of the compound shown by the following formula (M-1) (hereinafter may be referred to as "compound (M-1)"), 35.04 g (10 mol %) of the Compound (M-4) synthesized in Example 1, and 1.75 g (5 mol %) of dimethyl-2,2'-azobisisobutyrate (AIBN) (initiator) were dissolved in 100 g of methyl ethyl ketone to prepare a monomer solution. A three-necked flask (500 ml) equipped with a thermometer and a dropping funnel was charged with 50 g of methyl ethyl ketone, and purged with nitrogen for 30 minutes.

The inside of the flask was heated to 80° C. with stirring using a magnetic stirrer. The monomer solution was added dropwise to the flask over 3 hours using the dropping funnel. After the addition, the mixture was aged for 3 hours, and cooled to 30° C. or less to obtain a polymer solution. The polymer solution was added to 1000 g of methanol, and a precipitated white powder was collected by filtration. The white powder thus collected was washed twice with 200 g of methanol in a slurry state, collected again by filtration, and dried at 50° C. for 17 hours to obtain 32.15 g of a white powdery polymer (A-1) (yield: 64.3%).

The polymer (A-1) had an Mw of 5400 and a dispersity (Mw/Mn) of 1.28. The ratio of the content (mol %) of repeating units derived from the compound (M-1) to the content (mol %) of repeating units derived from the compound (M-4) determined by gas chromatography was 92.1/7.9. The polymer (A-1) is referred to as "fluorine-containing polymer (A-1)". Note that the compounds (M-1) and (M-4) were used in an amount of 50 g in total. The amount of each compound is based on the total amount of the compounds, and the amount of the initiator is based on the total amount of the compounds and the initiator.

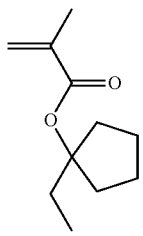

(M-1)

Examples 6 to 10

Production of Fluorine-Containing Polymers (A-2) to (A-6)

Fluorine-containing polymers (A-2) to (A-6) were produced in the same manner as in Example 5, with the exception that the compounds shown in Table 2 were used in amounts shown in Table 2. The Mw, the dispersity (Mw/Mn), and the yield (%) of each fluorine-containing polymer, and the ratio (mol %) of repeating units derived from each compound are shown in Table 3.

TABLE 2

| | Fluorine-containing polymer | Compound | | | | Initiator |
|---|---|---|---|---|---|---|
| | | Type | Content (mol %) | Type | Content (mol %) | Content (mol %) |
| Example 5 | A-1 | M-1 | 90 | M-4 | 10 | 5 |
| Example 6 | A-2 | M-1 | 80 | M-4 | 20 | 5 |
| Example 7 | A-3 | M-1 | 95 | M-4 | 5 | 5 |
| Example 8 | A-4 | M-1 | 90 | M-5 | 10 | 5 |
| Example 9 | A-5 | M-1 | 90 | M-6 | 10 | 5 |
| Example 10 | A-6 | M-1 | 90 | M-7 | 10 | 5 |

TABLE 3

| | Content (mol %) of repeating unit | | | | | Fluorine-containing polymer | | | |
|---|---|---|---|---|---|---|---|---|---|
| | M-1 | M-4 | M-5 | M-6 | M-7 | Type | Yield (%) | Mw | Mw/Mn |
| Example 5 | 92.1 | 7.9 | — | — | — | A-1 | 64.3 | 5400 | 1.28 |
| Example 6 | 84.4 | 15.6 | — | — | — | A-2 | 59.5 | 6000 | 1.25 |
| Example 7 | 96.8 | 3.2 | — | — | — | A-3 | 60.3 | 5200 | 1.29 |
| Example 8 | 91.2 | — | 8.8 | — | — | A-4 | 68.2 | 5500 | 1.28 |
| Example 9 | 90.1 | — | — | 9.9 | — | A-5 | 61.7 | 6100 | 1.25 |
| Example 10 | 90.4 | — | — | — | 9.6 | A-6 | 64.2 | 5600 | 1.30 |

A fluorine-containing polymer (A)-7' was produced in the same manner as in Example 5, except for using only the compound (a-1) as the monomer. The hydrogen atoms of some of the hydroxyl group included in the polymer (A)-7' were substituted with a methoxymethyl group via a reaction with chloromethoxymethane to obtain a polymer (A)-7. As a result of $^1$H-NMR analysis, it was found that 40 mol % of the hydrogen atoms of the hydroxyl groups included in the polymer (A)-7 were substituted with a methoxyethyl group.

Synthesis Example

Production of Acid-Labile Group-Containing Polymer (B-1)

21.5 g (50 mol %) of the compound shown by the following formula (M-2) (hereinafter may be referred to as "compound (M-2)") and 28.4 g (50 mol %) of the compound shown by the following formula (M-3) (hereinafter may be referred to as "compound (M-3)") were dissolved in 100 g of 2-butanone. 2.10 g of AIBN was added to the solution to prepare a monomer solution. A three-necked flask (500 ml) charged with 50 g of 2-butanone was purged with nitrogen for 30 minutes, and heated to 80° C. with stirring. The monomer solution was added dropwise to the flask using a dropping funnel over 3 hours.

The compounds were polymerized for 6 hours from the start of addition of the monomer solution. The polymer solution was cooled with water to 30° C. or less, and poured into 2000 g of methanol. A white powdery precipitate was collected by filtration. The white powder thus collected was washed twice with 400 g of methanol in a slurry state, collected again by filtration, and dried at 50° C. for 17 hours to obtain 38 g of a white powdery polymer (B-1) (yield: 76%). The polymer (B-1) had an Mw of 7200 and a dispersity (Mw/Mn) of 1.65. The ratio of the content (mol %) of repeating units derived from the compound (M-2) and the content (mol %) of repeating units derived from the compound (M-3) determined by $^{13}$C-NMR analysis was 50.2:49.8. The polymer (B-1) is referred to as "acid-labile group-containing polymer (B-1)". The content of low-molecular-weight components derived from the compounds in the polymer (B-1) was 0.03%.

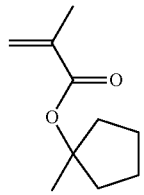

(M-2)

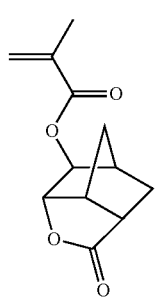

(M-3)

A radiation-sensitive resin composition including a polymer component including the fluorine-containing polymer was produced. A resist pattern was formed using the radiation-sensitive resin composition, and evaluated.

Example 11

Production of Radiation-Sensitive Resin Composition (1)

2.0 parts of the fluorine-containing polymer (A-1) obtained in Example 5, 100 parts of the acid-labile group-containing polymer (B-1) obtained in Synthesis Example, 9.6 parts of an acid generator (C-1), 0.65 parts of a nitrogen-containing compound (E-1), 1500 parts of a solvent (D-1), 650 parts of a solvent (D-2), and 30 parts of a solvent (D-3) were mixed to obtain a radiation-sensitive resin composition (1). The details of the acid generator (C-1), the nitrogen-containing compound (E-1), and the solvents (D-1) to (D-3) are given below.

Acid generator (C-1): compound shown by the following formula (C-1)

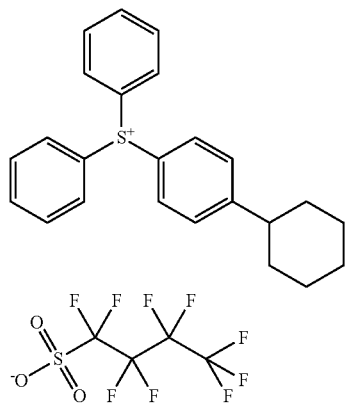

(C-1)

Solvent (D-1): propylene glycol monomethyl ether acetate (compound shown by the following formula (D-1))
Solvent (D-2): cyclohexanone (compound shown by the following formula (D-2))
Solvent (D-3): γ-butyrolactone (compound shown by the following formula (D-3))

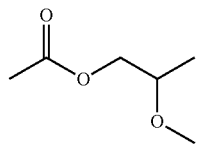

(D-1)

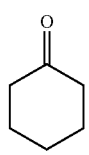

(D-2)

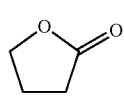

(D-3)

Nitrogen-containing compound (E-1): N-t-butoxycarbonyl-4-hydroxypiperidine (compound shown by the following formula (E-1))

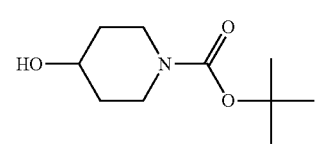

(E-1)

Examples 12 to 16 and Comparative Examples 1 and 2

Production of Radiation-Sensitive Resin Compositions (2) to (8)

Radiation-sensitive resin compositions (2) to (8) were produced in the same manner as in Example 11, except for changing the composition as shown in Table 4.

TABLE 4

|  | Fluorine-containing polymer | | Acid-labile group-containing polymer | | Acid generator | | Nitrogen-containing compound | | Solvent | |
|---|---|---|---|---|---|---|---|---|---|---|
|  | Type | Amount (parts) | Type | Amount (parts) | Type | Amount (parts) | Type | Amount (parts) | Type | Amount (parts) |
| Example 11 | A-1 | 2.0 | B-1 | 100 | C-1 | 9.6 | E-1 | 0.65 | D-1 D-2 D-3 | 1500 650 30 |
| Example 12 | A-2 | 1.5 | B-1 | 100 | C-1 | 9.6 | E-1 | 0.65 | D-1 D-2 D-3 | 1500 650 30 |
| Example 13 | A-3 | 2.5 | B-1 | 100 | C-1 | 9.6 | E-1 | 0.65 | D-1 D-2 D-3 | 1500 650 30 |
| Example 14 | A-4 | 2.0 | B-1 | 100 | C-1 | 9.6 | E-1 | 0.65 | D-1 D-2 D-3 | 1500 650 30 |
| Example 15 | A-5 | 2.0 | B-1 | 100 | C-1 | 9.6 | E-1 | 0.65 | D-1 D-2 D-3 | 1500 650 30 |

TABLE 4-continued

| | Fluorine-containing polymer | | Acid-labile group-containing polymer | | Acid generator | | Nitrogen-containing compound | | Solvent | |
|---|---|---|---|---|---|---|---|---|---|---|
| | Type | Amount (parts) | Type | Amount (parts) | Type | Amount (parts) | Type | Amount (parts) | Type | Amount (parts) |
| Example 16 | A-6 | 2.0 | B-1 | 100 | C-1 | 9.6 | E-1 | 0.65 | D-1 | 1500 |
| | | | | | | | | | D-2 | 650 |
| | | | | | | | | | D-3 | 30 |
| Comparative Example 1 | — | — | B-1 | 100 | C-1 | 9.6 | E-1 | 0.65 | D-1 | 1500 |
| | | | | | | | | | D-2 | 650 |
| | | | | | | | | | D-3 | 40 |
| Comparative Example 2 | A-7 | 2.0 | B-1 | 100 | C-1 | 9.6 | E-1 | 0.65 | D-1 | 1500 |
| | | | | | | | | | D-2 | 650 |
| | | | | | | | | | D-3 | 40 |

The following items (1) to (5) were evaluated (measured) using the radiation-sensitive resin compositions obtained in Examples 12 to 16 and Comparative Examples 1 and 2. The evaluation results are shown in Table 5.

(1) Evaluation of Elution Volume

As shown in FIG. 1, a square (30×30 cm) silicone rubber sheet 2 (manufactured by Kureha Elastomer Co., Ltd., thickness: 1.0 mm) having a circular opening (diameter: 11.3 cm) at the center was placed at the center of an 8-inch silicon wafer 1 (diameter: 20 cm) treated with hexamethyldisilazane (HMDS) (100° C., 60 sec) using a coater/developer "CLEAN TRACK ACT8" (manufactured by Tokyo Electron, Ltd.). Reference numeral 11 in FIG. 1 indicates a hexamethyldisilazane-treated layer.

Figure 2:
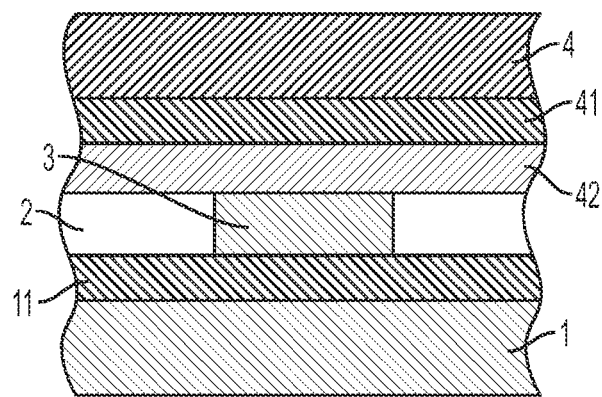
FIG. 2 is a partial schematic view showing an example of a state in which a resist film comes in contact with ultrapure water.

The center opening of the silicone rubber sheet 2 was filled with 10 ml of ultrapure water 3 using a 10 ml whole pipette. As shown in FIG. 2, an underlayer antireflective film ("ARC29A" manufactured by Bruwer Science) 41 (thickness: 77 nm) was formed using the coater/developer. The radiation-sensitive resin composition (Examples 11 to 16 and Comparative Examples 1 and 2) was spin-coated onto the underlayer antireflective film 41 using the coater/developer, and baked (115° C., 60 sec) to form a resist film 42 (thickness: 205 nm). The silicon wafer 4 was placed on the silicone rubber sheet 2 so that the surface of the resist film came in contact with the ultrapure water 3 and the ultrapure water 3 did not leak from the silicon rubber sheet 2. After 10 seconds had elapsed, the silicon wafer 4 was removed, and the ultrapure water 3 was collected using a glass syringe to obtain an analysis sample. The recovery rate of the ultrapure water 3 was 95% or more.

The peak intensity of the anion site of the acid generator (C-1) included in the ultrapure water was measured using a liquid chromatograph mass spectrometer (LC-MS) (LC section: "SERIES 1100" manufactured by AGILENT Corp., MS section: "Mariner" manufactured by PerSeptive Biosystems, Inc.) under the following conditions. The peak intensity of an aqueous solution (1 ppb, 10 ppb, or 100 ppb) of the acid generator (C-1) was measured under the following conditions, and a calibration curve was drawn. The elution volume of the acid generator (C-1) was calculated from the peak intensity using the calibration curve. Likewise, the peak intensity of an aqueous solution (1 ppb, 10 ppb, or 100 ppb) of the nitrogen-containing compound (E-1) was measured under the following measurement conditions, and a calibration curve was drawn. The elution volume of the nitrogen-containing compound (E-1) was calculated from the peak intensity using the calibration curve. A case where the elution volume was $5.0 \times 10^{-12}$ mol/cm$^2$/sec or more was evaluated as "Unacceptable", and a case where the elution volume was less than $5.0 \times 10^{-12}$ mol/cm$^2$/sec was evaluated as "Acceptable".

Measurement Conditions
Column: "CAPCELL PAK MG" (manufactured by Shiseido Co., Ltd.) (×1)
Flow rate: 0.2 ml/min
Eluant: mixture prepared by adding 0.1 mass % of formic acid to water/methanol (3/7) (mass ratio) mixture
Measurement temperature: 35° C.

(2) Receding Contact Angle

A film of the radiation-sensitive resin composition (Examples 11 to 16 and Comparative Examples 1 and 2) was formed on a substrate (wafer). The receding contact angle was immediately measured by the following method at a temperature of 23° C. (room temperature) and a humidity of 45% under atmospheric pressure using a contact angle meter ("DSA-10" manufactured by KRUS).

Specifically, the position of the wafer stage of the contact angle meter was adjusted, and the substrate was placed on the stage. After injecting water into the needle, the position of the needle was adjusted to the initial position at which a waterdrop can be formed on the substrate. Water was discharged from the needle to form a waterdrop (25 μl) on the substrate. After removing the needle, the needle was moved downward to the initial position, and introduced into the waterdrop. The waterdrop was sucked through the needle for 90 seconds at a rate of 10 μl/min, and the contact angle formed by the liquid surface and the substrate was measured every second (90 times in total). The average value of twenty contact angle measured values (20 seconds) after the measured value became stable was calculated, and taken as the receding contact angle.

(3) Sensitivity (mJ/cm$^2$)

A 12-inch silicon wafer on which the above lower-layer antireflective film (thickness: 77 nm) was formed on the surface was used as a substrate. The antireflective film was formed using the above coater/developer (see "(1) Evaluation of elution volume"). The radiation-sensitive resin composition (Examples 11 to 16 and Comparative Examples 1 and 2) was spin-coated onto the substrate using the coater/developer, and baked (PB) under the conditions shown in Table 5 to form a resist film (thickness: 120 nm).

The resist film was exposed via a mask pattern using an ArF excimer laser exposure system ("NSR S306C" manufactured by Nikon Corp., NA=0.78, σ=0.93/0.69). After performing PEB under conditions shown in Table 5, the resist film was developed at 23° C. for 30 seconds using a 2.38% tetramethylammonium hydroxide aqueous solution, washed with water, and dried to form a positive-tone resist pattern. An optimum dose at which a 1:1 line-and-space (1L1S) pattern having a line width of 90 nm was formed was taken as the sensitivity. A scanning electron microscope ("S-9380" manufactured by Hitachi High-Technologies Corporation) was used for the measurement.

(4) Evaluation of Cross-Sectional Shape (Pattern Shape) of Pattern

The cross-sectional shape of the 90 nm line-and-space pattern (see "(3) Sensitivity") was observed using a scanning electron microscope ("S-4800" manufactured by Hitachi High-Technologies Corporation). A case where the line-and-space pattern had a T-top shape (i.e., a shape other than a rectangular shape) was evaluated as "Unacceptable", and a case where the line-and-space pattern had a rectangular shape was evaluated as "Acceptable".

(5) Evaluation of Number of Defects

An 8-inch silicon wafer on which the above lower-layer antireflective film (thickness: 77 nm) was formed on the surface was used as a substrate. The antireflective film was formed using the above coater/developer (see "(1) Evaluation of elution volume"). The radiation-sensitive resin composition (Examples 11 to 16 and Comparative Examples 1 and 2) was spin-coated onto the substrate using the coater/developer, and baked (PB) under the conditions shown in Table 5 to form a resist film (thickness: 120 nm).

The resist film was rinsed with purified water for 90 seconds. The resist film was exposed through a mask pattern using the above ArF excimer laser exposure system (NA=0.78, σ=0.85, 1/2 Annular). The resist film was then rinsed with pure water for 90 seconds. After performing PEB under the conditions shown in Table 5, the resist film was developed at 23° C. for 60 seconds using a 2.38% tetramethylammonium hydroxide aqueous solution, washed with water, and dried to form a positive-tone resist pattern.

A hole pattern (width: 1000 nm) was formed over the entire wafer at an optimum dose at which a hole pattern having a width of 1000 nm was formed to obtain a defect inspection wafer. The measurement was performed using the above scanning electron microscope. The number of defects of the hole pattern (width: 1000 nm) was measured using a system "KLA2351" (manufactured by KLA Tencor Corp.).

Defects measured using the system "KLA2351" were observed using the above scanning electron microscope, and classified into a defect due to the resist and a defect due to foreign matter. A case where the number of defects due to the resist was 100 or more per wafer was evaluated as "Unacceptable", and a case where the number of defects due to the resist was less than 100 per wafer was evaluated as "Acceptable".

Note that the term "defect due to the resist" refers to a residual defect due to insufficient dissolution during development, a protrusion defect due to undissolved resin in the solvent, and the like, and the term "defect due to foreign matter" refers to a defect that occurs due to dust, uneven application, bubbles, or the like.

As is clear from Table 5, when using the radiation-sensitive resin compositions obtained in Examples 11 to 16, the elution volume into the immersion liquid during liquid immersion lithography was small, a high receding contact angle and an excellent pattern shape were obtained, and the number of defects was small. Therefore, the radiation-sensitive resin compositions obtained in Examples 11 to 16 are expected to be advantageous for advanced lithography. When using the radiation-sensitive resin composition obtained in Comparative Example 1, the elution volume upon contact with the immersion liquid during liquid immersion lithography was large, the receding contact angle was low, and a large number of defects were observed. When using the radiation-sensitive resin composition obtained in Comparative Example 2, the elution volume upon contact with the immersion liquid during liquid immersion lithography was equal to that when using the radiation-sensitive resin compositions obtained in Examples 11 to 16. However, the receding contact angle was low to some extent, and a large number of defects were observed.

The fluorine-containing polymer according to embodiments of the invention may be utilized for a lithographic process using deep ultraviolet rays, X-rays, electron beams, or the like as a light source. In particular, the fluorine-containing polymer may suitably be used as a polymer component of a radiation-sensitive resin composition that may suitably be used as a resist for forming a resist film used for liquid immersion lithography. Therefore, the fluorine-containing polymer and the radiation-sensitive resin composition may suitably be used for lithography for which a reduction in line width will be increasingly desired.

Obviously, numerous modifications and variations of the present invention are possible in light of the above teachings. It is therefore to be understood that within the scope of the appended claims, the invention may be practiced otherwise than as specifically described herein.

What is claimed is:

1. A compound having a general formula (1),

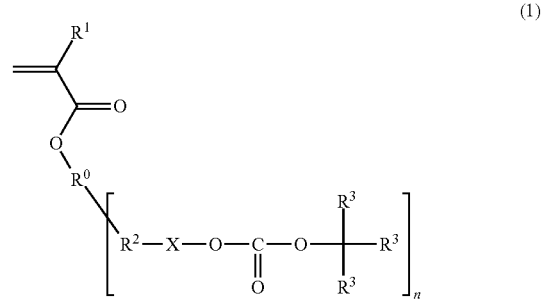

TABLE 5

| | (1) Elution volume | | | | | | | |
|---|---|---|---|---|---|---|---|---|
| | Acid generator | Nitrogen-containing compound | (2) Receding contact angle (°) | PB (temperature/time) | PEB (temperature/time) | (3) Sensitivity (mJ/cm$^2$) | (4) Cross-sectional shape of pattern | (5) Number of defects |
| Example 11 | Acceptable | Acceptable | 80.5 | 100° C./60 sec | 110° C./60 sec | 48 | Acceptable | Acceptable |
| Example 12 | Acceptable | Acceptable | 81.2 | 100° C./60 sec | 110° C./60 sec | 48 | Acceptable | Acceptable |
| Example 13 | Acceptable | Acceptable | 80.6 | 100° C./60 sec | 110° C./60 sec | 48 | Acceptable | Acceptable |
| Example 14 | Acceptable | Acceptable | 78.8 | 100° C./60 sec | 110° C./60 sec | 48 | Acceptable | Acceptable |
| Example 15 | Acceptable | Acceptable | 77.5 | 100° C./60 sec | 110° C./60 sec | 48 | Acceptable | Acceptable |
| Example 16 | Acceptable | Acceptable | 76.6 | 100° C./60 sec | 110° C./60 sec | 48 | Acceptable | Acceptable |
| Comparative Example 1 | Unacceptable | Unacceptable | 61.0 | 100° C./60 sec | 110° C./60 sec | 49 | Acceptable | Unacceptable |
| Comparative Example 2 | Acceptable | Acceptable | 74.2 | 100° C./60 sec | 110° C./60 sec | 48 | Acceptable | Unacceptable | wherein
  n is an integer from 2 to 5,
  $R^0$ represents an (n+1)-valent linear or branched aliphatic hydrocarbon group having 1 to 10 carbon atoms, or an (n+1)-valent alicyclic hydrocarbon group having 3 to 20 carbon atoms,
  $R^1$ represents a hydrogen atom, a methyl group, or a trifluoromethyl group,
  $R^2$ represents a single bond, a methylene group, an ethylene group, a 1-methylethylene group, a 2-methylethylene group, or a divalent alicyclic hydrocarbon group having 4 to 20 carbon atoms,
  each $R^2$ is a same as or different from each other,
  each $R^3$ independently represents a monovalent alicyclic hydrocarbon group having 4 to 20 carbon atoms or a linear or branched alkyl group having 1 to 4 carbon atoms, or
  each $R^3$ independently represents a monovalent alicyclic hydrocarbon group having 4 to 20 carbon atoms or a linear or branched alkyl group having 1 to 4 carbon atoms, and two of $R^3$ groups bond to form a divalent alicyclic hydrocarbon group having 4 to 20 carbon atoms together with the carbon atom bonded to the two of $R^3$ groups,
  X represents a linear or branched fluoroalkylene group having 1 to 10 carbon atoms, and
  each X is a same as or different from each other.

2. The compound according to claim 1, the compound being shown by a general formula (1a),

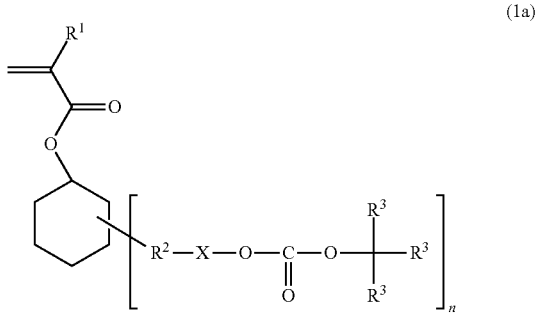

wherein
  n is an integer from 2 to 5,
  $R^1$ represents a hydrogen atom, a methyl group, or a trifluoromethyl group,
  $R^2$ represents a single bond, a methylene group, an ethylene group, a 1-methylethylene group, a 2-methylethylene group, or a divalent alicyclic hydrocarbon group having 4 to 20 carbon atoms,
  each $R^2$ is a same as or different from each other,
  each $R^3$ independently represents a monovalent alicyclic hydrocarbon group having 4 to 20 carbon atoms or a linear or branched alkyl group having 1 to 4 carbon atoms, or
  each $R^3$ independently represents a monovalent alicyclic hydrocarbon group having 4 to 20 carbon atoms or a linear or branched alkyl group having 1 to 4 carbon atoms, and two of $R^3$ groups bond to form a divalent alicyclic hydrocarbon group having 4 to 20 carbon atoms together with the carbon atom bonded to the two of $R^3$ groups,
  X represents a linear or branched fluoroalkylene group having 1 to 10 carbon atoms, and
  each X is a same as or different from each other.

3. A compound having a general formula (1),

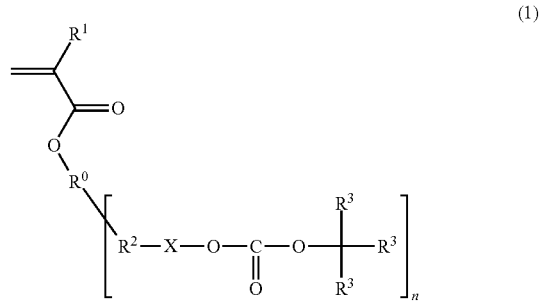

wherein
  n is 2,
  $R^0$ represents an (n+1)-valent linear or branched aliphatic hydrocarbon group having 1 to 10 carbon atoms, an (n+1)-valent alicyclic hydrocarbon group having 3 to 20 carbon atoms, or an (n+1)-valent aromatic hydrocarbon group having 6 to 20 carbon atoms,
  $R^1$ represents a hydrogen atom, a methyl group, or a trifluoromethyl group,
  $R^2$ represents a single bond, a methylene group, an ethylene group, a 1-methylethylene group, a 2-methylethylene group, or a divalent alicyclic hydrocarbon group having 4 to 20 carbon atoms,
  each $R^2$ is a same as or different from each other,
  each $R^3$ independently represents a monovalent alicyclic hydrocarbon group having 4 to 20 carbon atoms or a linear or branched alkyl group having 1 to 4 carbon atoms, or
  each $R^3$ independently represents a monovalent alicyclic hydrocarbon group having 4 to 20 carbon atoms or a linear or branched alkyl group having 1 to 4 carbon atoms, and two of $R^3$ groups bond to form a divalent alicyclic hydrocarbon group having 4 to 20 carbon atoms together with the carbon atom bonded to the two of $R^3$ groups,
  X represents a linear or branched fluoroalkylene group having 1 to 10 carbon atoms, and
  each X is a same as or different from each other.

4. The compound according to claim 3, the compound being shown by a general formula (1-2),

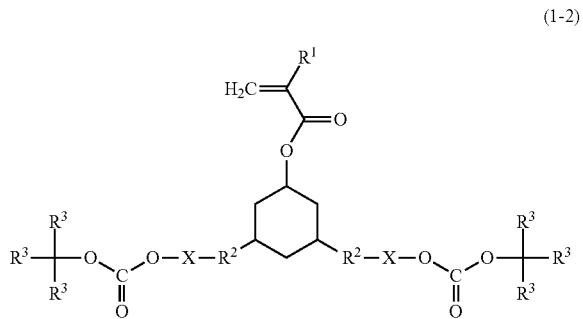

wherein
- $R^1$ represents a hydrogen atom, a methyl group, or a trifluoromethyl group,
- each $R^2$ independently represents a single bond, a methylene group, an ethylene group, a 1-methylethylene group, a 2-methylethylene group, or a divalent alicyclic hydrocarbon group having 4 to 20 carbon atoms,
- each $R^3$ independently represents a monovalent alicyclic hydrocarbon group having 4 to 20 carbon atoms or a linear or branched alkyl group having 1 to 4 carbon atoms, or
- each $R^3$ independently represents a monovalent alicyclic hydrocarbon group having 4 to 20 carbon atoms or a linear or branched alkyl group having 1 to 4 carbon atoms, and two of $R^3$ groups bond to form a divalent alicyclic hydrocarbon group having 4 to 20 carbon atoms together with the carbon atom bonded to the two of $R^3$ groups, and
- each X independently represents a linear or branched fluoroalkylene group having 1 to 10 carbon atoms.

5. A fluorine-containing polymer comprising a repeating unit (1) derived from the compound according to claim 1.

6. A fluorine-containing polymer comprising a repeating unit shown by a general formula (I),

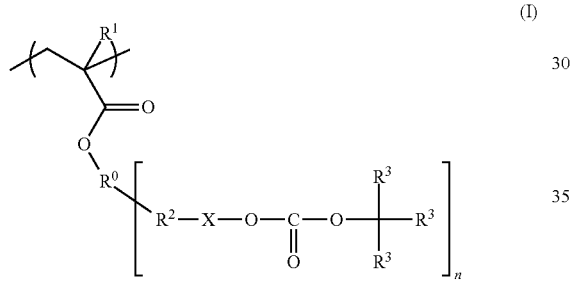

wherein
- n is an integer from 2 to 5,
- $R^0$ represents an (n+1)-valent linear or branched aliphatic hydrocarbon group having 1 to 10 carbon atoms, or an (n+1)-valent alicyclic hydrocarbon group having 3 to 20 carbon atoms,
- $R^1$ represents a hydrogen atom, a methyl group, or a trifluoromethyl group,
- $R^2$ represents a single bond, a methylene group, an ethylene group, a 1-methylethylene group, a 2-methylethylene group, or a divalent alicyclic hydrocarbon group having 4 to 20 carbon atoms,
- each $R^2$ is a same as or different from each other,
- each $R^3$ independently represents a monovalent alicyclic hydrocarbon group having 4 to 20 carbon atoms or a linear or branched alkyl group having 1 to 4 carbon atoms, or
- each $R^3$ independently represents a monovalent alicyclic hydrocarbon group having 4 to 20 carbon atoms or a linear or branched alkyl group having 1 to 4 carbon atoms, and two of $R^3$ groups bond to form a divalent alicyclic hydrocarbon group having 4 to 20 carbon atoms together with the carbon atom bonded to the two of $R^3$ groups,
- X represents a linear or branched fluoroalkylene group having 1 to 10 carbon atoms, and
- each X is a same as or different from each other.

7. The fluorine-containing polymer according to claim 6, wherein the repeating unit shown by the general formula (I) is a repeating unit shown by a general formula (Ia),

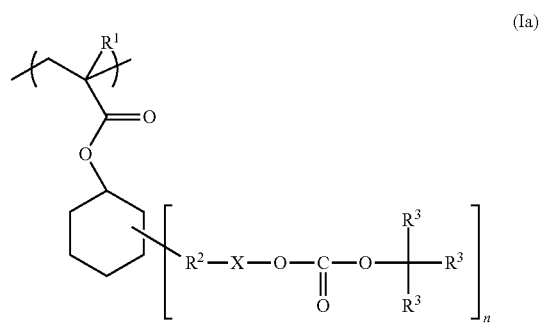

wherein
- n is an integer from 2 to 5,
- $R^1$ represents a hydrogen atom, a methyl group, or a trifluoromethyl group,
- $R^2$ represents a single bond, a methylene group, an ethylene group, a 1-methylethylene group, a 2-methylethylene group, or a divalent alicyclic hydrocarbon group having 4 to 20 carbon atoms,
- each $R^2$ is a same as or different from each other,
- each $R^3$ independently represents a monovalent alicyclic hydrocarbon group having 4 to 20 carbon atoms or a linear or branched alkyl group having 1 to 4 carbon atoms, or
- each $R^3$ independently represents a monovalent alicyclic hydrocarbon group having 4 to 20 carbon atoms or a linear or branched alkyl group having 1 to 4 carbon atoms, and two of $R^3$ groups bond to form a divalent alicyclic hydrocarbon group having 4 to 20 carbon atoms together with the carbon atom bonded to the two of $R^3$ groups,
- X represents a linear or branched fluoroalkylene group having 1 to 10 carbon atoms, and
- each X is a same as or different from each other.

8. The fluorine-containing polymer according to claim 7, wherein the repeating unit shown by the general formula (Ia) is a repeating unit shown by a general formula (I-2),

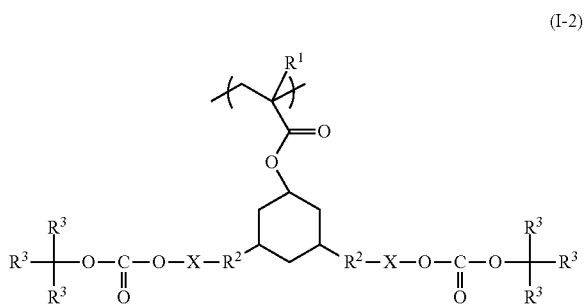

wherein
- $R^1$ represents a hydrogen atom, a methyl group, or a trifluoromethyl group,
- each $R^2$ independently represents a single bond, a methylene group, an ethylene group, a 1-methylethylene group, a 2-methylethylene group, or a divalent alicyclic hydrocarbon group having 4 to 20 carbon atoms, each R³ independently represents a monovalent alicyclic hydrocarbon group having 4 to 20 carbon atoms or a linear or branched alkyl group having 1 to 4 carbon atoms, or each R³ independently represents a monovalent alicyclic hydrocarbon group having 4 to 20 carbon atoms or a linear or branched alkyl group having 1 to 4 carbon atoms, and two of R³ groups bond to form a divalent alicyclic hydrocarbon group having 4 to 20 carbon atoms together with the carbon atom bonded to the two of R³ groups, and each X independently represents a linear or branched fluoroalkylene group having 1 to 10 carbon atoms.

9. A radiation-sensitive resin composition comprising:

(A) the fluorine-containing polymer according to claim 5, and (B) an acid-labile group-containing polymer, the acid-labile group-containing polymer excluding the fluorine-containing polymer (A).

10. The radiation-sensitive resin composition according to claim 9, wherein a content of the fluorine-containing polymer (A) in the composition is 0.1 to 40 parts by mass based on 100 parts by mass of the acid-labile group-containing polymer (B).

11. A method of producing a compound comprising reacting a compound shown by a general formula (1-0) with a compound shown by a general formula (0),

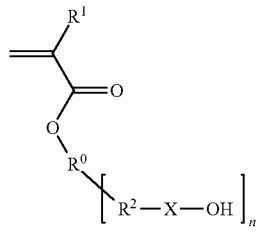

(1-0)

wherein n is an integer from 2 to 5,

R⁰ represents an (n+1)-valent linear or branched aliphatic hydrocarbon group having 1 to 10 carbon atoms, or an (n+1)-valent alicyclic hydrocarbon group having 3 to 20 carbon atoms, R¹ represents a hydrogen atom, a methyl group, or a trifluoromethyl group, R² represents a single bond, a methylene group, an ethylene group, a 1-methylethylene group, a 2-methylethylene group, or a divalent alicyclic hydrocarbon group having 4 to 20 carbon atoms, each R² is a same as or different from each other, X represents a linear or branched fluoroalkylene group having 1 to 10 carbon atoms, and each X is a same as or different from each other,

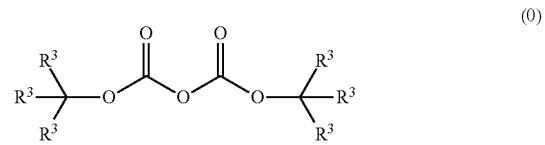

(0)

and wherein each R³ independently represents a monovalent alicyclic hydrocarbon group having 4 to 20 carbon atoms or a linear or branched alkyl group having 1 to 4 carbon atoms, or each R³ independently represents a monovalent alicyclic hydrocarbon group having 4 to 20 carbon atoms or a linear or branched alkyl group having 1 to 4 carbon atoms, and two of R³ groups bond to form a divalent alicyclic hydrocarbon group having 4 to 20 carbon atoms together with the carbon atom bonded to the two of R³ groups.

* * * * *